US011925659B2

(12) United States Patent
Hrynkow et al.

(10) Patent No.: US 11,925,659 B2
(45) Date of Patent: Mar. 12, 2024

(54) METHODS FOR TREATING ALZHEIMER'S DISEASE

(71) Applicant: Cyclo Therapeutics, Inc., Gainesville, FL (US)

(72) Inventors: Sharon H. Hrynkow, Annandale, VA (US); Jeffrey L. Tate, Newberry, FL (US); N. Scott Fine, Jupiter, FL (US)

(73) Assignee: Cyclo Therapeutics, Inc., Gainesville, FL (US)

( * ) Notice: Subject to any disclaimer, the term of this patent is extended or adjusted under 35 U.S.C. 154(b) by 430 days.

(21) Appl. No.: 17/289,137

(22) PCT Filed: Oct. 24, 2019

(86) PCT No.: PCT/US2019/057784
§ 371 (c)(1),
(2) Date: Apr. 27, 2021

(87) PCT Pub. No.: WO2020/092107
PCT Pub. Date: May 7, 2020

(65) Prior Publication Data
US 2022/0008453 A1  Jan. 13, 2022

Related U.S. Application Data

(60) Provisional application No. 62/885,053, filed on Aug. 9, 2019, provisional application No. 62/752,131, filed on Oct. 29, 2018.

(51) Int. Cl.
*A61K 31/724* (2006.01)
*A61K 45/06* (2006.01)
*A61K 47/10* (2017.01)

(52) U.S. Cl.
CPC ............ *A61K 31/724* (2013.01); *A61K 45/06* (2013.01); *A61K 47/10* (2013.01)

(58) Field of Classification Search
None
See application file for complete search history.

(56) References Cited

U.S. PATENT DOCUMENTS

| | | | |
|---|---|---|---|
| 4,877,778 A | 10/1989 | Carpenter et al. | |
| 5,569,756 A | 10/1996 | Qi et al. | |
| 8,883,494 B2 | 11/2014 | Khan | |
| 9,512,399 B2 | 12/2016 | Khan | |
| 9,675,634 B2 | 6/2017 | Machielse et al. | |
| 10,058,520 B2 | 8/2018 | Song et al. | |
| 10,517,900 B2 | 12/2019 | Khan | |
| 10,881,694 B2 | 1/2021 | Khan | |
| 11,020,422 B2 | 6/2021 | McKew et al. | |
| 2015/0065457 A1 | 3/2015 | Fornoni et al. | |
| 2018/0085392 A1 | 3/2018 | Gaspar et al. | |

FOREIGN PATENT DOCUMENTS

| | | |
|---|---|---|
| CA | 1222697 A | 6/1987 |
| DE | 3346123 A1 | 6/1985 |
| WO | WO-2015/087016 A1 | 6/2015 |
| WO | WO-2015/191931 A1 | 12/2015 |
| WO | WO-2016/201137 A1 | 12/2016 |
| WO | WO-2017/163128 A2 | 9/2017 |

OTHER PUBLICATIONS

Yao, Jiaqi, et al. "Neuroprotection by cyclodextrin in cell and mouse models of Alzheimer disease." Journal of Experimental Medicine 209.13 (2012): 2501-2513.*
Hall, Alicia M., and Erik D. Roberson. "Mouse models of Alzheimer's disease." Brain research bulletin 88.1 (2012): 3-12.*
Agola et al., "Rab GTPases as regulators of endocytosis, targets of disease and therapeutic opportunities" Clin Genet 2011, 80:305-318.
Brewster, Marcus, E., "Registration Experiences with Hydroxypropyl-β-cyclodextrin" Nordic Chapter Meeting of the Controlled Release Society (CRS) Reykjavik, Iceland, Jun. 2-5, 2012, pp. 1-74.
Bereznitski et al., "Thin-Layer Chromatography—A Useful Technique for the Separation of Enantiomers" Journal of AOAC International 84, No. 4, pp. 1242-1251 (2001).
Cortes et al., "TFEB dysregulation as a driver of autophagy dysfunction in neurodegenerative disease: Molecular mechanisms, cellular processes, andemerging therapeutic opportunities" Neurobiology of Disease 122 (2019) 83-93.
DuFour, et al., "Rapid quantification of 2-hydroxypropyl-β-cyclodextrin in liquid pharmaceutical formulations by 1H nuclear magnetic resonance spectroscopy" European Journal of Pharmaceutical Sciences 73 (2015) 20-28.
E. Grzadka., "Adsorption and electrokinetic properties in the system:Beta-cyclodextrin/alumina in the presence of ionic and non-ionic Surfactants" Colloids and Surfaces A: Physicochem. Eng. Aspects 481 (2015):261-268.
El-Beshbishi, S., et al. "Toxoplasmosis among Egyptian children with neurological disorders: developmental and risk factors analysis" Parasitologists United Journal, 13(3), 190-196 (2020).
Feringa et al., "Cholesterol and Alzheimer's Disease; From Risk Genes to Pathological Effects" Frontiers in Aging Neuroscience, 13(690372):1-17.
Silvia Pérez García., "Pharmacological experiment on neurodegeneration in mature trisomic mouse models" Bachelor's Thesis/ Biomedical Engineering, Universitat Pompeu Fabra, Barcelona (2021).
Gidwani et al., "A Comprehensive Review on Cyclodextrin-Based Carriers for Delivery of Chemotherapeutic Cytotoxic Anticancer Drugs" BioMed Research International 2015, Article ID 198268, pp. 1-15.
Hastings, et al., "Expanded access with intravenous hydroxypropyl-β-cyclodextrin to treat children and young adults with Neimann-Pick disease type C1: a case report analysis" Orphanet Journal of Rare Diseases (2019) 14:228, pp. 1-16.

(Continued)

*Primary Examiner* — Patrick T Lewis
(74) *Attorney, Agent, or Firm* — Goodwin Procter LLP

(57) ABSTRACT

Methods for the prevention or treatment of Alzheimer's disease in a human patient are disclosed comprising administering a hydroxypropyl-beta-cyclodextrin.

38 Claims, No Drawings

(56) References Cited

OTHER PUBLICATIONS

Kaukonen, Ann Marie., "Poorly water soluble substances: challenges, options and limitations for children" Finnish Medicines Agency, pp. 1-20 (2010).
Leduc et al., "APOE and cholesterol homeostatis in Alzheimer's disease" Trends in Molecular Medicine, 16(10) pp. 469-477 (2010).
Lieberman et al., "Autophagy in lysosomal storage disorders" Autophagy, Landesbioscience, 8:5, 719-730 (2012).
Liu et al., "Reversal of defective lysosomal transport in NPC disease ameliorates liver dysfunction and neurodegeneration in the npc1-/- mouse" PNAS, (2009) 106(7): 2377-2382.
Liu, Benny., "Therapeutic potential of cyclodextrins in the treatment of Niemann-Pick type C disease" Clin Lipidol Jun. 2012; 7(3): 289-301.
Liu et al., "Total flavonoid extract from *Dracoephalum moldavica* L. attenuates β-amyloid-induced toxicity through anti-amyloidogenesic and neurotrophic pathways" Life Sciences 193(2018) 214-225.
Malanga et al., ""Back to the Future": A New Look at Hydroxypropyl Beta-Cyclodextrins" Journal of Pharmaceutical Sciences 105 (2016) 2921-2931.
Malnar et al., "Bidirectional links between Alzheimer's disease and Niemann-Pick type C disease" Neurobiology of Disease 72 (2014) 37-47.
Massey et al., "Targeting DYRK1A/B kinases to modulate p21-cyclin D1-p27 signalling and induce anti-tumour activity in a model of human glioblastoma" J. Cell Mol Med. 2021;25:10650-10662.
Matsuo et al., "Effects of cyclodextrin in two patients with Niemann-Pick Type C disease" Molecular Genetics and Metabolism 108 (2013) 76-81.
Matsuo et al., "Effects of intracerebroventricular administration of 2-hydroxypropyl-β-cyclodextrin in a patient with Niemann-Pick Type C disease" Molecular Genetics and Metabolism Reports 1 (2014) 391-400.
McAlary et al., "Emerging Developments in Targeting Proteotoxicityin Neurodegenerative Diseases" CNS Drugs (2019) 33:883-904.
Nawa et al., "Elimination of protein aggregates prevents premature senescence in human trisomy 21 fibroblasts" PLOS ONE14(7):1-24 (2019).
Nixon, Ralph A., "The role of autophagy in neurodegenerative Disease" Nature Medicine, 19(8) (2013).
Noguera, Cèsar Sierra., "Transcriptomic and Cognitive Interplay in Down Syndrome" Tesi Doctoral UPF / 2021, Department Cex-Upf-PhD Programme in Biomedicine, Universitat Pompeu Fabra Barcelona, pp. 1-163.
Patel et al., "Development and Evaluation of In Situ Gelling System for Treatment of Periodontitis" Am. J. PharmTech Res. 2012; 2(4).
Peric et al., "Early etiology of Alzheimer's disease: tipping the balance toward autophagy or endosomal dysfunction?" Acta Neuropathol (2015) 129:363-381.
Anonymous., "Public summary of opinion on orphan designation Hydroxy-propyl-beta-cyclodextrin for the treatment of Niemann-Pick disease, type C" European Medicines Agency, Committee for Orphan Medicinal Products, Mar. 12, 2015.
Pitha et al., "Hydroxypropyl-β-cyclodextrin: preparation and characterization; effects on solubility of drugs" International Journal of Pharmaceutics, 29 (1986) 73-82.
Singh et al., "A Patent Review on Nanotechnology-Based Nose-to-Brain Drug Delivery" Recent Patents on Nanotechnology, 2020, 14:174-192.
Stensen et al., "Novel DYRK1A Inhibitor Rescues Learning and Memory Deficits in a Mouse Model of Down Syndrome" Pharmaceuticals 2021, 14, 1170.
Szente et al., "Analytical characterization of cyclodextrins: History, official methods and recommended new techniques" Journal of Pharmaceutical and Biomedical Analysis 130 (2016) 347-365.
Thomas et al., "The State of Innovation in Highly Prevalent Chronic Diseases Volume IV: Alzheimer's Disease Therapeutics" Biotechnology Innovation Organization, BIO Industry Analysis (year) pp. 1-19, downloaded from: www.bio.org/iareports <http://www.bio.org/iareports>.
Van Karnebeek et al., Treatment of Neurogenetic Developmental Conditions: From 2016 into the Future Pediatric Neurology 65 (2016) 1-13.
Vázquez-Oliver et al., "Long-term decreased cannabinoid type-1 receptor activity restores specific neurological phenotypes in the Ts65Dn mouse model of Down syndrome" Laboratory of Neuropharmacology-NeuroPhar. Department of Experimental and Health Sciences, preprint, https://doi.org/10.1101/2021.11.22. 469296; this version posted Nov. 22, 2021.
Vanier, Marie T., "Neimann-Pick disease type C" Orphanet Journal of Rare Diseases 2010, 5:16.
Eldholm et al., "Progression of Alzheimer's Disease: A Longitudinal Study in Norwegian Memory Clinics" Journal of Alzheimer's Disease 61 (2018) 1221-1232.
Rassu et al., "Hydroxypropyl-ß-Cyclodextrin Formulated in Nasal Chitosan Microspheres as Candidate Therapeutic Agent in Alzheimer's Disease" Current Drug Delivery, 2018, 15:746-748.
Suh et al., "A longitudinal study of Alzheimer's disease: rates of cognitive and functional decline" Int J Geriatr Psychiatry 2004; 19: 817-824.
Van der Vlies et al., "Most rapid cognitive decline in APOE ϵ4 negative Alzheimer's disease with early onset" Psychological Medicine (2009) 39:1907-1911.
Yalcin et al., "Neuroprotective Effects of Engineered Polymeric Nasal Microspheres Containing Hydroxypropyl-ß-cyclodextrin on ß-Amyloid (1-42)-Induced Toxicity" Journal of Pharmaceutical Sciences vol. 105, Issue 8, Aug. 2016, pp. 2372-2380.
Bai Ping Ren et al. "HP-[beta]-cyclodextrin as an inhibitor of amyloid-[beta] aggregation and toxicity", Physical Chemistry Chemical Physics, vol. 18, No. 30, Jan. 1, 2016 (Jan. 1, 2016), pp. 20476-20485.
International Search Report dated Jan. 27, 2020 for PCT Application No. PCT/US2019/057784, 4 pages.
Open-Label Study of Long-Term Safety and Efficacy of Intravenous Trappsol Cyclo (HP[beta]CD) in Niemann-Pick Disease Type C, Internet Mar. 28, 2019 (Mar. 28, 2019), p. 1-7, https://clinicaltrials.gov/ct2/show/record/NCT03893071?view=record.
Roquette's Kleptose HPB, Internet Oct. 1, 2017 (Oct. 1, 2017), p. 1-2, https://www.roquette.com/-/media/roquette-sharepoint-libraries/marcomonline---pharma/roquette-pharma-injectable-dialysis-sell-sheets-kleptose-hpb-lb.pdf.
Written Opinion of the International Searching Authority dated Jan. 27, 2020 for PCT Application No. PCT/US2019/057784, 6 pages.
Yao et al. "Neuroprotection by cyclodextrin in cell and mouse models of Alzheimer disease" J. Exp. Med. 2012 vol. 209 No. 13, pp. 2501-2513.
Barbero-Camps et al., "Cholesterol impairs autophagy-mediated clearance of amyloid beta while promoting its secretion" Autophagy, 2018, 14(7), pp. 1129-1154.
Coisne et al., "Cyclodextrins as Emerging Therapeutic Tools in the Treatment of Cholesterol-Associated Vascular and Neurodegenerative Diseases" Molecules, 2016, 21(12), 1748 (22 pages).
Yang et al., "Cyclodextrin has conflicting actions on autophagy flux in vivo in brains of normal and Alzheimer model mice" Human Molecular Genetics, 2017, 26(5), pp. 843-859.
Yalcin et al., "Potential protective effects of hydroxypropyl-β-cyclodextrin on Aβ (1-42)-induced neurotoxicity" Free Radical Biology and Medicine, 2018, 120(P-114), pp. S45-S166.
Gavini et al., "Mucoadhesive microspheres for nasal administration of cyclodextrins" Journal of Drug Targeting, 2009, 17(2), pp. 168-179.
Muramatsu et al., "Prevalence and Comorbidity of Anxiety and Depressive Disorders in Studies of PRIME-MD and PHQ (Patient Health Questionnaire) in Japan" Anxiety Disorders, 2021, pp. 2-14.
Ohnishi et al., "Drug Therapy for Dementia" Illustrated "Dementia" Series No. 3, IRYO, 2017, 71(3) pp. 132-137.

\* cited by examiner

METHODS FOR TREATING ALZHEIMER'S DISEASE

CROSS-REFERENCE

This application is a § 371 National Stage Application of PCT/US2019/057784, filed Oct. 24, 2019, and claims the benefit of, and priority to, U.S. Provisional Application No. 62/752,131, filed Oct. 29, 2018, and U.S. Provisional Application No. 62/885,053, filed Aug. 9, 2019, each of which are incorporated herein by reference in their entirety.

BACKGROUND

It is estimated that there are over 50 million people currently living with dementia worldwide. In the United States alone, there are approximately 5.5 million patients currently suffering from Alzheimer's disease (AD) and this number is expected to rise to 13.8 million by 2050. The global cost of AD and other forms of dementia is currently estimated to be $605 billion.

Current approved therapeutics for the treatment of AD (e.g., cholinesterase inhibitors and memantine) have limited efficacy and do not halt disease progression or reverse the disease process as they do not treat the underlying mechanisms responsible for AD development.

More recently, drug development for the treatment of AD has shifted focus to limit, prevent and mitigate amyloid beta (Aβ) and Tau accumulation. Amyloid-based therapies include increasing Aβ clearance, decreasing Aβ aggregation as well as targeted Aβ immunotherapy. To date, despite multiple attempts, these drugs have largely failed in late-stage clinical trials. Tau-based therapies have focused on targeting tau phosphorylation, preventing tau oligomerization, microtubule stabilization and tau immunotherapy. Like Aβ therapies, to date while Tau-based therapies have shown some promise these therapies are still in early phases of development and will not yield efficacy data for several years.

As such there remains a pressing need to develop new treatments for AD that target the underlying mechanisms of AD and lead to a halt in the progression of the disease and/or a reversal of the disease process.

SUMMARY

In one aspect, the invention provides methods for treating Alzheimer's disease in a human patient suffering from Alzheimer's disease comprising administering an effective amount of a hydroxypropyl-beta-cyclodextrin composition. In some embodiments, the human patient suffering from Alzheimer's disease may be at least 50 years old, at least 60 years old, at least 65 years old, at least 70 years old, or at least 80 years old.

A contemplated method for treating Alzheimer's disease in a human patient suffering from Alzheimer's disease may further comprise administering the hydroxypropyl-beta-cyclodextrin composition in a dose amount of 500 mg/kg to 3000 mg/kg by parenteral administration or 100 mg to 750 mg by central nervous system (CNS) directed administration (intrathecally or intracerebroventricularly) at intervals selected to insure patient safety. For example, the method can comprise administering the hydroxypropyl-beta-cyclodextrin composition in a monthly dose amount selected from the group consisting of 500 mg/kg, 1,000 mg/kg, 1,500 mg/kg, 2,000 mg/kg, 2,500 mg/kg and 3,000 mg/kg.

In some embodiments, an effective amount of a hydroxypropyl-beta-cyclodextrin composition, as described herein, may be administered to a human patient suffering from Alzheimer's disease weekly, twice a month, or once a month. In some embodiments, an effective amount of a hydroxypropyl-beta-cyclodextrin composition, as described herein, may be administered to a human patient suffering from Alzheimer's disease intravenously, subcutaneously, by intrathecal administration, or by intracerebroventricular administration.

A contemplated method for treating Alzheimer's disease in a human patient suffering from Alzheimer's disease may further comprise administering the hydroxypropyl-beta-cyclodextrin composition in a monthly escalating dose regimen at intervals selected to insure patient safety. For example, the method can comprise administering the hydroxypropyl-beta-cyclodextrin composition in an amount of 500 mg/kg during month one and month 2, 1,000 mg/kg during months 3 and 4, 1,500 mg/kg during months 5 and 6, 2,000 mg/kg during months 7 and 8 and 2,500 mg/kg during months 9 and 10, until a maximum tolerated dose is determined, and subsequently administering the maximum tolerated dose.

In some embodiments, the method of treating Alzheimer's disease in a human patient suffering from Alzheimer's disease may further comprise administering a second therapeutic agent. In some embodiments, the second therapeutic agent is an agent indicated to treat Alzheimer's disease. In some embodiments, the second therapeutic agent is selected from the group consisting of donepezil, rivastigmine, galantamine, memantine, verubecestat, solanezumab, bapineuzumab, aducanumab, tideglusib, epothilone D and ABBV-8E12. In some embodiments, the second therapeutic agent selected from the group consisting of a cholinesterase inhibitor, an NMDA receptor antagonist, a humanized antibody which targets tau protein, a humanized antibody which targets amyloid beta protein, and a BACE inhibitor.

In some embodiments, a hydroxypropyl-beta-cyclodextrin composition of the present invention may comprise a mixture of two or more hydroxypropyl-beta-cyclodextrin species, wherein each of the two or more hydroxypropyl-beta-cyclodextrin species has a different degree of hydroxypropylation of the cyclodextrin ring, and wherein the mixture of two or more hydroxypropyl-beta-cyclodextrin species has a molar substitution value from about 0.59 to about 0.73. In some embodiments, the hydroxypropyl-beta-cyclodextrin composition comprises 2.5% w/w or less of propylene glycol. In some embodiments, the hydroxypropyl-beta-cyclodextrin composition comprises 0.15% w/w or less of unsubstituted beta-cyclodextrin.

In another aspect, provided herein is a method of treating Alzheimer's disease in a human patient suffering from Alzheimer's disease, the method comprising administering to the human patient an effective amount of a hydroxypropyl-beta-cyclodextrin composition, wherein the hydroxypropyl-beta-cyclodextrin composition comprises a mixture of two or more hydroxypropyl-beta-cyclodextrin species, and wherein mixture of two or more hydroxypropyl-beta-cyclodextrin species has a molar substitution value from about 0.59 to about 0.73.

In another aspect, provided herein is a method of treating Alzheimer's disease in a human patient suffering from Alzheimer's disease, the method comprising:
(a) administering to the human patient an initial 500 mg/kg dose of a hydroxypropyl-beta-cyclodextrin composition; and (b) administering to the human patient the hydroxypropyl-beta-cyclodextrin composition in a monthly escalating dose regimen until a maximum tolerated dose is determined. For example, the monthly escalating dose regimen can comprise administering to the human patient a 500 mg/kg dose one month after the initial dose, 1,000 mg/kg doses two and three months after the initial dose, 1,500 mg/kg doses four and five months after the initial dose, 2,000 mg/kg doses 6 and 7 months after the initial dose and 2,500 mg/kg doses 8 and 9 months after the initial dose.

DETAILED DESCRIPTION

The present disclosure provides, in part, a method for treating Alzheimer's disease in a subject suffering from Alzheimer's disease (AD), wherein the subject is administered an effective amount of a hydroxypropyl-beta-cyclodextrin composition. The hydroxypropyl-beta-cyclodextrin compositions of the present disclosure may, for example, be administered to the subject parenterally (e.g., subcutaneously or intravenously) or via CNS (e.g., intrathecally or intracerebroventricularly) using a fixed or escalating monthly dosing regimen. Administration of such hydroxypropyl-beta-cyclodextrin compositions may stabilize AD progression and/or reverse key features of the disease (e.g., impaired cognitive function).

Unless defined otherwise, all technical and scientific terms used herein have the same meaning as commonly understood by one of ordinary skill in the art to which this invention belongs. The abbreviations used herein have their conventional meaning within the chemical and biological arts.

Throughout the description, where compositions and kits are described as having, including, or comprising specific components, it is contemplated that, additionally, there are compositions and kits of the present invention that consist essentially of, or consist of, the recited components.

In the application, where an element or component is said to be included in and/or selected from a list of recited elements or components, it should be understood that the element or component can be any one of the recited elements or components, or the element or component can be selected from a group consisting of two or more of the recited elements or components.

Further, it should be understood that elements and/or features of a composition or a method described herein can be combined in a variety of ways without departing from the spirit and scope of the present invention, whether explicit or implicit herein. For example, where reference is made to a particular compound, that compound can be used in various embodiments of compositions of the present invention and/or in methods of the present invention, unless otherwise understood from the context. In other words, within this application, embodiments have been described and depicted in a way that enables a clear and concise application to be written and drawn, but it is intended and will be appreciated that embodiments may be variously combined or separated without parting from the present teachings and invention(s). For example, it will be appreciated that all features described and depicted herein can be applicable to all aspects of the invention(s) described and depicted herein.

It should be understood that the order of steps or order for performing certain actions is immaterial so long as the present invention remain operable. Moreover, two or more steps or actions may be conducted simultaneously.

At various places in the present specification, variable or parameters are disclosed in groups or in ranges. It is specifically intended that the description include each and every individual subcombination of the members of such groups and ranges. For example, an integer in the range of 0 to 40 is specifically intended to individually disclose 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, and 40, and an integer in the range of 1 to 20 is specifically intended to individually disclose 1, 2, 3, 4, 5, 6, 7, 8, 9, 10, 11, 12, 13, 14, 15, 16, 17, 18, 19, and 20.

The use of any and all examples, or exemplary language herein, for example, "such as" or "including," is intended merely to illustrate better the present invention and does not pose a limitation on the scope of the invention unless claimed. No language in the specification should be construed as indicating any non-claimed element as essential to the practice of the present invention.

Definitions

The articles "a" and "an" are used in this disclosure to refer to one or more than one (i.e., to at least one) of the grammatical object of the article, unless the context is inappropriate. By way of example, "an element" means one element or more than one element.

The term "and/or" is used in this disclosure to mean either "and" or "or" unless indicated otherwise.

It should be understood that the expression "at least one of" includes individually each of the recited objects after the expression and the various combinations of two or more of the recited objects unless otherwise understood from the context and use. The expression "and/or" in connection with three or more recited objects should be understood to have the same meaning unless otherwise understood from the context.

The use of the term "include," "includes," "including," "have," "has," "having," "contain," "contains," or "containing," including grammatical equivalents thereof, should be understood generally as open-ended and non-limiting, for example, not excluding additional unrecited elements or steps, unless otherwise specifically stated or understood from the context.

As used herein, the term "about" means approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 10%.

"Individual," "patient," and "subject" are used interchangeably and include any animal, including mammals, e.g., mice, rats, other rodents, rabbits, dogs, cats, swine, cattle, sheep, horses, or primates, including humans.

The terms "treat", "treating" or "treatment" includes any effect, for example, lessening, reducing, modulating, ameliorating or eliminating, that results in the improvement of the condition, disease, disorder, and the like, or ameliorating a symptom thereof. Treating can be curing, improving, or at least partially ameliorating the disorder. In certain embodiments, treating is curing the disease.

"Pharmaceutically acceptable" includes molecular entities and formulations that do not produce an adverse, allergic or other untoward reaction when administered to an animal, or a human, as appropriate. For human administration, preparations should meet sterility, pyrogenicity, and general safety and purity standards as required by FDA Office of Biologics standards.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The pharmaceutical formulations of the disclosure can be administered to a mammal, such as a human, but can also be administered to other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the disclosure is desirably a mammal in which treatment of Alzheimer's disease is desired.

As used herein, "pharmaceutical composition" or "pharmaceutical formulation" refers to the combination of an active agent with a carrier, inert or active, making the composition especially suitable for diagnostic or therapeutic use in vivo or ex vivo.

As used herein, "effective amount" or "therapeutically-effective amount" refers to the amount of a compound or composition (e.g., a compound or composition of the present invention) sufficient to effect beneficial or desired results. An effective amount can be administered in one or more administrations, applications or dosages and is not intended to be limited to a particular formulation or administration route.

As used herein, "administering" means oral administration, administration as a suppository, topical contact, intravenous, parenteral, intraperitoneal, intramuscular, intralesional, intrathecal, intracranial, intracerebroventricular, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arterial, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies (e.g., anti-cancer agent, chemotherapeutic, or treatment for a neurodegenerative disease). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation).

As used herein, "hydroxypropyl-beta-cyclodextrin species", "beta-cyclodextrin species", or "beta-cyclodextrins" may refer to a beta-cyclodextrin molecule with a unique chemical composition and/or chemical structure. For example, a hydroxypropyl-beta-cyclodextrin species of the present invention may have unique properties including, but not limited to, average number of hydroxypropyl groups per beta-cyclodextrin molecule, molar substitution value, distribution of hydroxypropyl groups, degree of distribution of hydroxypropyl groups, or any combination thereof.

As used herein, "substituted at one or more hydroxyl positions by hydroxypropyl groups" refers to replacement of the hydrogen of one or more hydroxyl groups of a beta-cyclodextrin molecule with a hydroxypropyl group or a hydroxypropyl oligomer. For instance, "substituted at one or more hydroxyl positions by hydroxypropyl groups" can refer to an insertion of one or more $CH_2CH(CH_3)O$— substituents within one or more O—H bonds on a beta-cyclodextrin molecule resulting in one or more ether linkages.

As used herein, the "cognitive function" or "cognitive functioning" of a subject may be defined as an intellectual activity or process. Examples of intellectual activities or processes include, but are not limited to, attention, processing speed, learning and memory, executive function, verbal fluency and working memory. For example, a hydroxypropyl-beta-cyclodextrin composition of the present invention may improve cognitive function if it improves one or more intellectual activities or processes in a subject with Alzheimer's disease.

Hydroxypropyl-Beta-Cyclodextrins

Cyclodextrins are naturally occurring cyclic oligosaccharides derived from the enzymatic conversion of starch and can also be synthetically manufactured. Cyclodextrins are composed of a variable number of glucopyranose units that can form a hollow cone-like toroid structure consisting of a hydrophobic cavity and hydrophilic exterior. The hollow cone-like toroid structure may also be referred to as "beta-cyclodextrin ring". The number of glucopyranose determines the cavity size and nomenclature of cyclodextrins, with the most common consisting of six, seven, or eight glucopyranose units and named α-, β-, and γ-cyclodextrin, respectively. The unique structure of cyclodextrins allows them to form water-soluble complexes with otherwise insoluble hydrophobic compounds. This property of cyclodextrins has led to their application as drug delivery vehicles to improve solubility, stability, and bioavailability of many pharmacologically active agents. Hydroxypropyl-beta-cyclodextrin (HPβCD), which is also known as and may be referred to herein as 2-hydroxypropyl-beta-cyclodextrin, is a highly soluble, chemically modified synthetic derivative of beta-cyclodextrin. HPβCD is one of the most commonly used and least toxic derivatives of a naturally occurring cyclodextrin for drug delivery.

In one aspect, provided herein are hydroxypropyl-beta-cyclodextrin compositions for the treatment of Alzheimer's disease in a subject suffering from Alzheimer's disease. In certain embodiments the subject is a human patient.

In certain embodiments, a hydroxypropyl-beta-cyclodextrin composition of the present invention is a mixture of hydroxypropyl-beta-cyclodextrin species. In some embodiments, the mixture of hydroxypropyl-beta-cyclodextrin species comprises a mixture of beta-cyclodextrin molecules substituted at one or more hydroxyl positions by hydroxypropyl groups.

In certain embodiments, the hydroxypropyl-beta-cyclodextrin composition comprises a mixture of two or more hydroxypropyl-beta-cyclodextrin species. In some embodiments, the hydroxypropyl-beta-cyclodextrin composition comprises a mixture of 2, 3, 4, 5, 6, 7, 8, 9, 10, 11, 12, 13, 14, 15, 16, 17, 18, 19, or 20 hydroxypropyl-beta-cyclodextrin species. In some embodiments, each of the two or more hydroxypropyl-beta-cyclodextrin species in the mixture has a different degree of hydroxypropylation of the beta-cyclodextrin ring.

In certain embodiments, a hydroxypropyl-beta-cyclodextrin species in the mixture comprises glucose units of the structure:

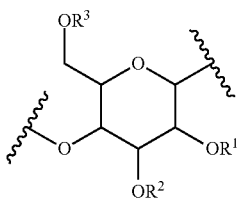

wherein $R^1$, $R^2$, and $R^3$, independently for each occurrence, are H or HP, wherein HP comprises one or more hydroxypropyl groups.

In certain embodiments, HP comprises 1, 2, 3, 4, 5, 6, 7, 8, 9, or 10 hydroxypropyl groups. In some embodiments, HP comprises one hydroxypropyl group. In certain embodiments, HP consists of 1, 2, 3, 4, 5, 6, 7, 8, 9, or 10 hydroxypropyl groups. In some embodiments, HP consists of one hydroxypropyl group.

In certain embodiments, the average number of occurrences of HP per beta-cyclodextrin ring is about 3 to about 7, about 3 to about 6, about 3 to about 5, about 3 to about 4, about 4 to about 7, about 4 to about 6, about 4 to about 5, about 5 to about 7, about 5 to about 6, or about 6 to about 7. In certain embodiments, the average number of occurrences of HP per beta-cyclodextrin ring is about 3, about 4, about 5, about 6, or about 7.

In certain embodiments, the total occurrences of $R^3$=HP are greater than the total occurrences of either $R^1$=HP or $R^2$=HP. In certain embodiments, the total occurrences of $R^3$=HP are greater than the total combined occurrences of $R^1$=HP and $R^2$=HP.

In certain embodiments, at least about 5%, at least about 10%, at least about 15%, at least about 20%, at least about 25%, at least about 30%, at least about 35%, at least about 40%, or at least about 45% of the total combined occurrences of $R^1$ and $R^2$ are HP.

In some embodiments, not more than about 50%, not more than about 55%, not more than about 60%, not more than about 65%, not more than about 70%, not more than about 75%, not more than about 80%, not more than about 85%, not more than about 90%, or not more than about 95% of the total combined occurrences of $R^1$ and $R^2$ are HP.

In certain embodiments, the percentage of $R^1$ and $R^2$ combined that are HP ranges from about 5% to about 95%, about 10% to about 95%, about 15% to about 95%, about 20% to about 95%, about 25% to about 95%, about 30% to about 95%, about 35% to about 95%, about 40% to about 95%, about 45% to about 95%, about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; about 5% to about 90%, about 10% to about 90%, about 15% to about 90%, about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%; about 5% to about 85%, about 10% to about 85%, about 15% to about 85%, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 80% to about 85%; about 5% to about 80%, about 10% to about 80%, about 15% to about 80%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%; about 5% to about 75%, about 10% to about 75%, about 15% to about 75%, about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%; about 5% to about 70%, about 10% to about 70%, about 15% to about 70%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%; about 5% to about 65%, about 10% to about 65%, about 15% to about 65%, about 20% to about 65%, about 25% to about 65%, about 30% to about 65%, about 35% to about 65%, about 40% to about 65%, about 45% to about 65%, about 50% to about 65%, about 55% to about 65%, about 60% to about 65%; about 5% to about 60%, about 10% to about 60%, about 15% to about 60%, about 20% to about 60%, about 25% to about 60%, about 30% to about 60%, about 35% to about 60%, about 40% to about 60%, about 45% to about 60%, about 50% to about 60%, about 55% to about 60%; about 5% to about 55%, about 10% to about 55%, about 15% to about 55%, about 20% to about 55%, about 25% to about 55%, about 30% to about 55%, about 35% to about 55%, about 40% to about 55%, about 45% to about 55%, about 50% to about 55%; about 5% to about 50%, about 10% to about 50%, about 15% to about 50%, about 20% to about 50%, about 25% to about 50%, about 30% to about 50%, about 35% to about 50%, about 40% to about 50%, about 45% to about 50%; about 5% to about 45%, about 10% to about 45%, about 15% to about 45%, about 20% to about 45%, about 25% to about 45%, about 30% to about 45%, about 35% to about 45%, about 40% to about 45%; about 5% to about 40%, about 10% to about 40%, about 15% to about 40%, about 20% to about 40%, about 25% to about 40%, about 30% to about 40%, about 35% to about 40%; about 5% to about 35%, about 10% to about 35%, about 15% to about 35%, about 20% to about 35%, about 25% to about 35%, about 30% to about 35%; about 5% to about 30%, about 10% to about 30%, about 15% to about 30%, about 20% to about 30%, about 25% to about 30%; about 5% to about 25%, about 10% to about 25%, about 15% to about 25%, about 20% to about 25%; about 5% to about 20%, about 10% to about 20%, about 15% to about 20%; about 5% to about 15%, about 10% to about 15%; or about 5% to about 10%.

In certain embodiments, at least about 5%, at least about 10%, at least about 15%, at least about 20%, at least about 25%, at least about 30%, at least about 35%, at least about 40%, at least about 45%, or at least about 50% of occurrences of $R^3$ are HP.

In certain embodiments, not more than about 55%, not more than about 60%, not more than about 65%, not more than about 70%, not more than about 75%, not more than about 80%, not more than about 85%, not more than about 90%, or not more than about 95% of occurrences of $R^3$ are HP.

In certain embodiments, the percentage of occurrence of $R^3$ that are HP ranges from about 20% to about 90%, about 25% to about 90%, about 30% to about 90%, about 35% to about 90%, about 40% to about 90%, about 45% to about 90%, about 50% to about 90%, about 55% to about 90%, about 60% to about 90%, about 65% to about 90%, about 70% to about 90%, about 75% to about 90%, about 80% to about 90%, about 85% to about 90%, about 20% to about 85%, about 25% to about 85%, about 30% to about 85%, about 35% to about 85%, about 40% to about 85%, about 45% to about 85%, about 50% to about 85%, about 55% to about 85%, about 60% to about 85%, about 65% to about 85%, about 70% to about 85%, about 75% to about 85%, about 80% to about 85%, about 20% to about 80%, about 25% to about 80%, about 30% to about 80%, about 35% to about 80%, about 40% to about 80%, about 45% to about 80%, about 50% to about 80%, about 55% to about 80%, about 60% to about 80%, about 65% to about 80%, about 70% to about 80%, about 75% to about 80%, about 20% to about 75%, about 25% to about 75%, about 30% to about 75%, about 35% to about 75%, about 40% to about 75%, about 45% to about 75%, about 50% to about 75%, about 55% to about 75%, about 60% to about 75%, about 65% to about 75%, about 70% to about 75%, about 20% to about 70%, about 25% to about 70%, about 30% to about 70%, about 35% to about 70%, about 40% to about 70%, about 45% to about 70%, about 50% to about 70%, about 55% to about 70%, about 60% to about 70%, about 65% to about 70%, about 20% to about 65%, about 25% to about 65%, about 30% to about 65%, about 35% to about 65%, about 40% to about 65%, about 45% to about 65%, about 50% to about 65%, about 55% to about 65%, about 60% to about 65%, about 20% to about 60%, about 25% to about 60%, about 30% to about 60%, about 35% to about 60%, about 40% to about 60%, about 45% to about 60%, about 50% to about 60%, about 55% to about 60%, about 20% to about 55%, about 25% to about 55%, about 30% to about 55%, about 35% to about 55%, about 40% to about 55%, about 45% to about 55%, about 50% to about 55%, about 20% to about 50%, about 25% to about 50%, about 30% to about 50%, about 35% to about 50%, about 40% to about 50%, about 45% to about 50%, about 20% to about 45%, about 25% to about 45%, about 30% to about 45%, about 35% to about 45%, about 40% to about 45%, about 5% to about 40%, about 10% to about 40%, about 15% to about 40%, about 20% to about 40%, about 25% to about 40%, about 30% to about 40%, about 35% to about 40%, about 20% to about 35%, about 25% to about 35%, about 30% to about 35%, about 20% to about 30%, about 25% to about 30%, or about 20% to about 25%.

In certain embodiments, at least about 70%, at least about 75%, at least about 80%, at least about 85%, at least about 90%, or at least about 95%, of the beta-cyclodextrins collectively have an average number of occurrences of HP per beta-cyclodextrin of about 4 to about 7, about 4 to about 6, about 4 to about 5, about 5 to about 7, about 5 to about 6, or about 6 to about 7.

In some embodiments, the percentage of beta-cyclodextrins that collectively have an average number of occurrences of HP per beta-cyclodextrin of about 4 to about 7, about 4 to about 6, about 4 to about 5, about 5 to about 7, about 5 to about 6, or about 6 to about 7, ranges from about 50% to about 99%, about 55% to about 99%, about 60% to about 99%, about 65% to about 99%, about 70% to about 99%, about 75% to about 99%, about 80% to about 99%, about 85% to about 99%, about 90% to about 99%, about 95% to about 99%, about 50% to about 97%, about 55% to about 97%, about 60% to about 97%, about 65% to about 97%, about 70% to about 97%, about 75% to about 97%, about 80% to about 97%, about 85% to about 97%, about 90% to about 97%, about 95% to about 97%, about 50% to about 95%, about 55% to about 95%, about 60% to about 95%, about 65% to about 95%, about 70% to about 95%, about 75% to about 95%, about 80% to about 95%, about 85% to about 95%, about 90% to about 95%, about 50% to about 90%, about 55% to about 90%, about 60% to about 90%, about 65% to about 90%, about 70% to about 90%, about 75% to about 90%, about 80% to about 90%, about 85% to about 90%, about 50% to about 85%, about 55% to about 85%, about 60% to about 85%, about 65% to about 85%, about 70% to about 85%, about 75% to about 85%, about 80% to about 85%, about 50% to about 80%, about 55% to about 80%, about 60% to about 80%, about 65% to about 80%, about 70% to about 80%, about 75% to about 80%, about 50% to about 75%, about 55% to about 75%, about 60% to about 75%, about 65% to about 75%, about 70% to about 75%, about 50% to about 70%, about 55% to about 70%, about 60% to about 70%, about 65% to about 70%, about 50% to about 65%, about 55% to about 65%, about 60% to about 65%, about 50% to about 60%, about 55% to about 60%, or about 50% to about 55%.

As used herein, the "degree of substitution" or "DS" refers to the total number of hydroxypropyl groups substituted directly or indirectly on a beta-cyclodextrin molecule. For example, a beta-cyclodextrin molecule containing glucose units, each of which is substituted with one hydroxypropyl group, has a DS=7. In another example, a beta-cyclodextrin molecule in which only one of the seven glucose units is substituted with a hydroxypropyl group, and that hydroxypropyl group is itself substituted with another hydroxypropyl group (e.g., a beta-cyclodextrin with a single occurrence of HP that comprises two hydroxypropyl groups), has a DS=2.

As used herein, the "average number of hydroxypropyl groups per beta-cyclodextrin," also known as an "average degree of substitution," "average DS," or "$DS_a$," refers to the total number of hydroxypropyl groups in a population of beta-cyclodextrins divided by the number of beta-cyclodextrin molecules. In an illustrative example, an equal parts mixture of beta-cyclodextrins containing glucose units that are each substituted with one hydroxypropyl group and beta-cyclodextrins containing glucose units that are each substituted with two hydroxypropyl groups has a $DS_a$=10.5 (average of equal parts beta-cyclodextrins with DS=7 and DS=14). In another illustrative example, a mixture of 33.3% beta-cyclodextrins in which only one of the seven glucose units is substituted with a hydroxypropyl group (DS=1) and 66.7% beta-cyclodextrins containing glucose units that are each substituted with one hydroxypropyl group (DS=7) has a $DS_a$=5.0. The $DS_a$ may be determined by multiplying the molar substitution by 7. As used herein. $DS_a$ is used synonymously with "degree of substitution" as that term is defined in the USP Hydroxypropyl Betadex monograph.

In certain embodiments, the hydroxypropyl-beta-cyclodextrin compositions of the present invention comprise a mixture of unsubstituted beta-cyclodextrin molecules and beta-cyclodextrin species substituted at one or more hydroxyl positions by hydroxypropyl groups, wherein the mixture has an average number of hydroxypropyl groups per beta-cyclodextrin molecule ($DS_a$) of about 3 to about 7, of about 3 to about 6, about 3 to about 5, about 3 to about 4, about 4 to about 7, about 4 to about 6, about 4 to about 5, about 5 to about 7, about 5 to about 6, or about 6 to about 7.

The distribution of the degree of substitution within the hydroxypropyl-beta-cyclodextrin compositions of the present invention comprising a mixture of unsubstituted beta-cyclodextrin molecules and beta-cyclodextrin species substituted at one or more hydroxyl positions by hydroxypropyl groups can vary. For example, an equal parts mixture of beta-cyclodextrins containing glucose units each of which is substituted with one hydroxypropyl group and beta-cyclodextrins containing glucose units each of which is substituted with two hydroxypropyl groups has a $DS_a$=10.5 (average of equal parts beta-cyclodextrins with DS=7 and DS=14). Although $DS_a$=10.5, in this example there are no beta-cyclodextrins having DS=10 or DS=11 within the mixture. In other cases, the majority of beta-cyclodextrin species within the mixture of beta-cyclodextrins have DS that are close to the $DS_a$.

In certain embodiments, at least about 50%, at least about 55%, about 60%, about 65%, about 70%, about 75%, about 80%, about 85%, about 90%, about 95%, or about 97%, of the beta-cyclodextrins within the mixture have a DS within $DS_a \pm X\sigma$, wherein $\sigma$ is the standard deviation, and X is 1, 2, or 3.

In certain embodiments, at least about 50% of the beta-cyclodextrins within the mixture have a DS within $DS_a \pm 1\sigma$. In some embodiments, about 55%, about 60%, about 65%, about 70%, about 75%, about 80%, about 85%, about 90%, about 95%, or about 97%, of the beta-cyclodextrins within the mixture have a DS within $DS_a \pm 1\sigma$.

In certain embodiments, at least about 50% of the beta-cyclodextrins within the mixture have a DS within $DS_a \pm 2\sigma$. In some embodiments, about 55%, about 60%, about 65%, about 70%, about 75%, about 80%, about 85%, about 90%, about 95%, or about 97%, of the beta-cyclodextrins within the mixture have a DS within $DS_a \pm 2\sigma$.

In certain embodiments, at least about 50% of the beta-cyclodextrins within the mixture have a DS within $DS_a \pm 3\sigma$. In some embodiments, about 55%, about 60%, about 65%, about 70%, about 75%, about 80%, about 85%, about 90%, about 95%, or about 97%, of the beta-cyclodextrins within the mixture have a DS within $DS_a \pm 3\sigma$.

In certain embodiments, at least about 50% of the beta-cyclodextrins have a DS within $DS_a \pm 0.8$. In some embodiments, about 55%, about 60%, about 65%, about 70%, about 75%, about 80%, about 85%, about 90%, about 95%, or about 97%, of the beta-cyclodextrins have a DS within $DS_a \pm 1$.

In certain embodiments, at least about 50% of the beta-cyclodextrins have a DS within $DS_a \pm 0.8$. In some embodiments, about 55%, about 60%, about 65%, about 70%, about 75%, about 80%, about 85%, about 90%, about 95%, or about 97%, of the beta-cyclodextrins have a DS within $DS_a \pm 0.8$.

In certain embodiments, at least about 50% of the beta-cyclodextrins have a DS within $DS_a \pm 0.6$. In some embodiments, about 55%, about 60%, about 65%, about 70%, about 75%, about 80%, about 85%, about 90%, about 95%, or about 97%, of the beta-cyclodextrins have a DS within $DS_a \pm 0.6$.

In certain embodiments, at least about 50% of the beta-cyclodextrins have a DS within $DS_a \pm 0.5$. In some embodiments, about 55%, about 60%, about 65%, about 70%, about 75%, about 80%, about 85%, about 90%, about 95%, or about 97%, of the beta-cyclodextrins have a DS within $DS_a \pm 0.5$.

In certain embodiments, at least about 50% of the beta-cyclodextrins have a DS within $DS_a \pm 0.4$. In some embodiments, about 55%, about 60%, about 65%, about 70%, about 75%, about 80%, about 85%, about 90%, about 95%, or about 97%, of the beta-cyclodextrins have a DS within $DS_a \pm 0.4$.

In certain embodiments, at least about 50% of the beta-cyclodextrins have a DS within $DS_a \pm 0.3$. In some embodiments, about 55%, about 60%, about 65%, about 70%, about 75%, about 80%, about 85%, about 90%, about 95%, or about 97%, of the beta-cyclodextrins have a DS within $DS_a \pm 0.3$.

In certain embodiments, at least about 50% of the beta-cyclodextrins have a DS within $DS_a \pm 0.2$. In some embodiments, about 55%, about 60%, about 65%, about 70%, about 75%, about 80%, about 85%, about 90%, about 95%, or about 97%, of the beta-cyclodextrins have a DS within $DS_a \pm 0.2$.

In certain embodiments, at least about 50% of the beta-cyclodextrins have a DS within $DS_a \pm 0.1$. In some embodiments, about 55%, about 60%, about 65%, about 70%, about 75%, about 80%, about 85%, about 90%, about 95%, or about 97%, of the beta-cyclodextrins have a DS within $DS_a \pm 0.1$.

The number of hydroxypropyl groups per anhydroglucose unit in the mixture of beta-cyclodextrins is known as the "molar substitution", or "MS", and may be determined according to the procedures set forth in the USP monograph on Hydroxypropyl Betadex (USP NF 2015) ("USP Hydroxypropyl Betadex monograph"), incorporated herein by reference in its entirety. In this disclosure, the term "average molar substitution", or "$MS_a$", is used synonymously with "MS" as that term is used in the USP Hydroxypropyl Betadex monograph, and the term "glucose unit" is used as a synonym for "anhydroglucose unit" as that term is used in the USP Hydroxypropyl Betadex monograph.

In some embodiments, the MS of the mixture of hydroxypropyl-beta-cyclodextrin species is from about 0.51 to about 0.75, about 0.51 to about 0.73, about 0.51 to about 0.71, about 0.51 to about 0.69, about 0.51 to about 0.67, about 0.51 to about 0.65, about 0.51 to about 0.63, about 0.51 to about 0.61, about 0.51 to about 0.59, about 0.51 to about 0.57, about 0.51 to about 0.55, about 0.51 to about 0.53, 0.53 to about 0.75, about 0.53 to about 0.73, about 0.53 to about 0.71, about 0.53 to about 0.69, about 0.53 to about 0.67, about 0.53 to about 0.65, about 0.53 to about 0.63, about 0.53 to about 0.61, about 0.53 to about 0.59, about 0.53 to about 0.57, about 0.53 to about 0.55, 0.55 to about 0.75, about 0.55 to about 0.73, about 0.55 to about 0.71, about 0.55 to about 0.69, about 0.55 to about 0.67, about 0.55 to about 0.65, about 0.55 to about 0.63, about 0.55 to about 0.61, about 0.55 to about 0.59, about 0.55 to about 0.57, 0.57 to about 0.75, about 0.57 to about 0.73, about 0.57 to about 0.71, about 0.57 to about 0.69, about 0.57 to about 0.67, about 0.57 to about 0.65, about 0.57 to about 0.63, about 0.57 to about 0.61, about 0.57 to about 0.59, 0.59 to about 0.75, about 0.59 to about 0.73, about 0.59 to about 0.71, about 0.59 to about 0.69, about 0.59 to about 0.67, about 0.59 to about 0.65, about 0.59 to about 0.63, about 0.59 to about 0.61, 0.61 to about 0.75, about 0.61 to about 0.73, about 0.61 to about 0.71, about 0.61 to about 0.69, about 0.61 to about 0.67, about 0.61 to about 0.65, about 0.61 to about 0.63, 0.63 to about 0.75, about 0.63 to about 0.73, about 0.63 to about 0.71, about 0.63 to about 0.69, about 0.63 to about 0.67, about 0.63 to about 0.65, 0.65 to about 0.75, about 0.65 to about 0.73, about 0.65 to about 0.71, about 0.65 to about 0.69, about 0.65 to about 0.67, 0.67 to about 0.75, about 0.67 to about 0.73, about 0.67 to about 0.71, about 0.67 to about 0.69, 0.69 to about 0.75, about 0.69 to about 0.73, about 0.69 to about 0.71, 0.71 to about 0.75, about 0.71 to about 0.73, or about 0.73 to about 0.75. In some embodiments, the MS of the mixture of hydroxypropyl-beta-cyclodextrin species is from about 0.59 to about 0.73.

In certain embodiments, the MS of the mixture of hydroxypropyl-beta-cyclodextrin species is about 0.40, about 0.41, about 0.42, about 0.43, about 0.44, about 0.45, about 0.46, about 0.47, about 0.48, about 0.49, about 0.50, about 0.51, about 0.52, about 0.53, about 0.54, about 0.55, about 0.56, about 0.57, about 0.58, about 0.59, about 0.60, about 0.61, about 0.62, about 0.63, about 0.64, about 0.65, about 0.66, about 0.69, about 0.68, about 0.69, about 0.70, about 0.71, about 0.72, about 0.73, about 0.74, about 0.75, about 0.76, about 0.77, about 0.78, about 0.79, or about 0.80. In some embodiments, the MS of the mixture of hydroxypropyl-beta-cyclodextrin species is about 0.59, about 0.60, about 0.61, about 0.62, about 0.63, about 0.64, about 0.65, about 0.66, about 0.69, about 0.68, about 0.69, about 0.70, about 0.71, about 0.72, or about 0.73.

Hydroxypropyl groups can be bonded to the beta-cyclodextrins as monomers, or can themselves be sequentially bonded to one or more additional hydroxypropyl groups to form hydroxypropyl oligomers which are then bonded to the beta-cyclodextrins. In certain embodiments, the hydroxypropyl groups are substituted at the hydroxyl positions of the beta-cyclodextrins as hydroxypropyl chains of the structure —[CH$_2$CH(CH$_3$)O]H, wherein n≥1 and the average number of hydroxypropyl chains per beta-cyclodextrin is from about 3 to about 7. In some embodiments, the average number of hydroxypropyl chains per beta-cyclodextrin is from about 3 to about 6, about 3 to about 5, about 3 to about 4, about 4 to about 7, about 4 to about 6, about 4 to about 5, about 5 to about 7, about 5 to about 6, or about 6 to about 7. In some embodiments, n is 1, 2, 3 or 4.

In one illustrative example, a hydroxypropyl chain of the structure —CH$_2$CH(CH$_3$)OH includes one hydroxypropyl group in the hydroxypropyl chain (n=1). In another illustrative example a hydroxypropyl chain of the structure —[CH$_2$CH(CH$_3$)O]$_3$H includes three hydroxypropyl groups in the hydroxypropyl chain (n=3).

In certain embodiments, the average number of hydroxypropyl chains per beta-cyclodextrin is 3.3±0.3, 3.4±0.3, 3.6±0.3, or 3.8±0.3. In certain embodiments, the average number of hydroxypropyl chains per beta-cyclodextrin is 4.0±0.3, 4.2±0.3, 4.4±0.3, 4.6±0.3, or 4.8±0.3. In certain embodiments, the average number of hydroxypropyl chains per beta-cyclodextrin is 5.0±0.3, 5.2±0.3, 5.4±0.3, 5.6±0.3, or 5.8±0.3. In certain embodiments, the average number of hydroxypropyl chains per beta-cyclodextrin is 6.0±0.3, 6.2±0.3, 6.4±0.3, 6.6±0.3, or 6.7±0.3.

In certain embodiments, the average number of hydroxypropyl chains per beta-cyclodextrin is 3.2±0.2, 3.3±0.2, 3.4±0.2, 3.5±0.2, 3.6±0.2, 3.7±0.2, or 3.8±0.2. In certain embodiments, the average number of hydroxypropyl chains per beta-cyclodextrin is 4.0±0.2, 4.1±0.2, 4.2±0.2, 4.3±0.2, 4.4±0.2, 4.5±0.2, 4.6±0.2, 4.7±0.2, or 4.8±0.2. In certain embodiments, the average number of hydroxypropyl chains per beta-cyclodextrin is 5.0±0.2, 5.1±0.2, 5.2±0.2, 5.3±0.2, 5.4±0.2, 5.5±0.2, 5.6±0.2, 5.7±0.2, or 5.8±0.2. In certain embodiments, the average number of hydroxypropyl chains per beta-cyclodextrin is 6.0±0.2, 6.1±0.2, 6.2±0.2, 6.3±0.2, 6.4±0.2, 6.5±0.2, 6.6±0.2, 6.7±0.2, or 6.8±0.2.

In certain embodiments, the average number of hydroxypropyl chains per beta-cyclodextrin is 3.1±0.1, 3.2±0.1, 3.3±0.1, 3.4±0.1, 3.5±0.1, 3.6±0.1, 3.7±0.1, 3.8±0.1, or 3.9±0.1. In certain embodiments, the average number of hydroxypropyl chains per beta-cyclodextrin is 4.0±0.1, 4.1±0.1, 4.2±0.1, 4.3±0.1, 4.4±0.1, 4.5±0.1, 4.6±0.1, 4.7±0.1, 4.8±0.1, or 4.9±0.1. In certain embodiments, the average number of hydroxypropyl chains per beta-cyclodextrin is 5.0±0.1, 5.1±0.1, 5.2±0.1, 5.3±0.1, 5.4±0.1, 5.5±0.1, 5.6±0.1, 5.7±0.1, 5.8±0.1, or 5.9±0.1. In certain embodiments, the average number of hydroxypropyl chains per beta-cyclodextrin is 6.0±0.1, 6.1±0.1, 6.2±0.1, 6.3±0.1, 6.4±0.1, 6.5±0.1, 6.6±0.1, 6.7±0.1, 6.8±0.1, or 6.9±0.1.

In certain embodiments, at least about 50% of the hydroxypropyl chains have n=1. In some embodiments, about 55%, about 60%, about 65%, about 70%, about 75%, about 80%, about 85%, about 90%, about 95%, or about 97%, of the hydroxypropyl chains have n=1. In some embodiments, at least 70% of the hydroxypropyl chains have n=1. In some embodiments, at least 90% of the hydroxypropyl chains have n=1.

In certain embodiments, percentage of the hydroxypropyl chains that have n=1 ranges from about 50% to about 99%, such as about 55% to about 99%, about 60% to about 99%, about 65% to about 99%, about 70% to about 99%, about 75% to about 99%, about 80% to about 99%, about 85% to about 99%, about 90% to about 99%, about 95% to about 99%; such as from about 50% to about 97%, such as about 55% to about 97%, about 60% to about 97%, about 65% to about 97%, about 70% to about 97%, about 75% to about 97%, about 80% to about 97%, about 85% to about 97%, about 90% to about 97%, about 95% to about 97%; such as from about 50% to about 95%, about 55% to about 95%, about 60% to about 95%, about 65% to about 95%, about 70% to about 95%, about 75% to about 95%, about 80% to about 95%, about 85% to about 95%, about 90% to about 95%; such as from about 50% to about 90%, about 55% to about 90%, about 60% to about 90%, about 65% to about 90%, about 70% to about 90%, about 75% to about 90%, about 80% to about 90%, about 85% to about 90%; such as from about 50% to about 85%, about 55% to about 85%, about 60% to about 85%, about 65% to about 85%, about 70% to about 85%, about 75% to about 85%, about 80% to about 85%; such as from about 50% to about 80%, about 55% to about 80%, about 60% to about 80%, about 65% to about 80%, about 70% to about 80%, about 75% to about 80%; such as from about 50% to about 75%, about 55% to about 75%, about 60% to about 75%, about 65% to about 75%, about 70% to about 75%; such as from about 50% to about 70%, about 55% to about 70%, about 60% to about 70%, about 65% to about 70%; such as from about 50% to about 65%, about 55% to about 65%, about 60% to about 65%; such as from about 50% to about 60%, about 55% to about 60%; or such as from about 50% to about 55%.

In certain embodiments, less than about 3%, less than about 5%, less than about 10%, less than about 15%, less than about 20%, less than about 25%, less than about 30%, less than about 35%, less than about 40%, less than about 45%, or less than about 50%, of the hydroxypropyl chains have n=2. In some embodiments, less than about 30% of the hydroxypropyl chains have n=2. In some embodiments, less than 10% of the hydroxypropyl chains have n=2.

In certain embodiments, the percentage of the hydroxypropyl chains that have n=2 ranges from about 5% to about 50%, such as about 10% to about 50%, about 15% to about 50%, about 20% to about 50%, about 25% to about 50%, about 30% to about 50%, about 35% to about 50%, about 40% to about 50%, about 45% to about 50%; such as from about 5% to about 45%, about 10% to about 45%, about 15% to about 45%, about 20% to about 45%, about 25% to about 45%, about 30% to about 45%, about 35% to about 45%, about 40% to about 45%; such as from about 5% to about 40%, about 10% to about 40%, about 15% to about 40%, about 20% to about 40%, about 25% to about 40%, about 30% to about 40%, about 35% to about 40%; such as from about 5% to about 35%, about 10% to about 35%, about 15% to about 35%, about 20% to about 35%, about 25% to about 35%, about 30% to about 35%; such as from about 5% to about 30%, about 10% to about 30%, about 15% to about 30%, about 20% to about 30%, about 25% to about 30%; such as from about 5% to about 25%, about 10% to about 25%, about 15% to about 25%, about 20% to about 25%; such as from about 5% to about 20%, about 10% to about 20%, about 15% to about 20%; such as from about 5% to about 15%, about 10% to about 15%; or about 5% to about 10%.

In some embodiments, less than about 3%, less than about 5%, less than about 10%, less than about 15%, less than about 20%, less than about 25%, less than about 30%, less than about 35%, less than about 40%, less than about 45%, or less than about 50%, of the hydroxypropyl chains have n>2. In some embodiments, less than about 10% of the hydroxypropyl chains have n>2.

In certain embodiments, the percentage of the hydroxypropyl chains that have n>2 ranges from about 5% to about 50%, about 10% to about 50%, about 15% to about 50%, about 20% to about 50%, about 25% to about 50%, about 30% to about 50%, about 35% to about 50%, about 40% to about 50%, about 45% to about 50%, about 5% to about 45%, about 10% to about 45%, about 15% to about 45%, about 20% to about 45%, about 25% to about 45%, about 30% to about 45%, about 35% to about 45%, about 40% to about 45%, about 5% to about 40%, about 10% to about 40%, about 15% to about 40%, about 20% to about 40%, about 25% to about 40%, about 30% to about 40%, about 35% to about 40%, about 5% to about 35%, about 10% to about 35%, about 15% to about 35%, about 20% to about 35%, about 25% to about 35%, about 30% to about 35%, about 5% to about 30%, about 10% to about 30%, about 15% to about 30%, about 20% to about 30%, about 25% to about 30%, about 5% to about 25%, about 10% to about 25%, about 15% to about 25%, about 20% to about 25%, about 5% to about 20%, about 10% to about 20%, about 15% to about 20%, about 5% to about 15%, about 10% to about 15%, or about 5% to about 10%.

In certain embodiments, the average number of hydroxypropyl chains per beta-cyclodextrin is from about 4 to about 6. In some embodiments, at least about 60% of the beta-cyclodextrins collectively have an average number of hydroxypropyl chains per beta-cyclodextrin of from about 4 to about 6. In some embodiments, at least about 65%, at least about 70%, at least about 75%, at least about 80%, at least about 85%, at least about 90%, at least about 95%, or at least about 97%, of the beta-cyclodextrins collectively have an average number of hydroxypropyl chains per beta-cyclodextrin of from about 4 to about 6. In some embodiments, the percentage of the beta-cyclodextrins that collectively have an average number of hydroxypropyl chains per beta-cyclodextrin of from about 4 to about 6 ranges from about 60% to about 97%, about 65% to about 97%, about 70% to about 97%, about 75% to about 97%, about 80% to about 97%, about 85% to about 97%, about 90% to about 97%, about 60% to about 95%, about 65% to about 95%, about 70% to about 95%, about 75% to about 95%, about 80% to about 95%, about 85% to about 95%, about 90% to about 95%, about 60% to about 90%, about 65% to about 90%, about 70% to about 90%, about 75% to about 90%, about 80% to about 90%, about 85% to about 90%, about 60% to about 85%, about 65% to about 85%, about 70% to about 85%, about 75% to about 85%, about 80% to about 85%, about 60% to about 80%, about 65% to about 80%, about 70% to about 80%, about 75% to about 80%, about 60% to about 75%, about 65% to about 75%, about 70% to about 75%, about 60% to about 70%, about 65% to about 70%, or about 60% to about 65%.

In certain embodiments, the hydroxypropyl-beta-cyclodextrin compositions as described herein comprise less than about 0.05% w/w, less than about 0.06% w/w, less than about 0.07% w/w, less than about 0.08% w/w, less than about 0.09% w/w, less than about 0.1% w/w, less than about 0.2% w/w, less than about 0.3% w/w, less than about 0.4% w/w, less than about 0.5% w/w, less than about 0.6% w/w, less than about 0.7% w/w, less than about 0.8% w/w, less than about 0.9% w/w, less than about 1.0% w/w, less than about 1.1% w/w, less than about 1.2% w/w, less than about 1.3% w/w, less than about 1.4% w/w, less than about 1.5% w/w, less than about 1.6% w/w, less than about 1.7% w/w, less than about 1.8% w/w, less than about 1.9% w/w, or less than about 2% w/w, of unsubstituted beta-cyclodextrin. In some embodiments, the hydroxypropyl-beta-cyclodextrin composition comprises less than about 0.15% w/w of unsubstituted beta-cyclodextrin.

In certain embodiments, the amount of unsubstituted beta-cyclodextrin in the hydroxypropyl-beta-cyclodextrin compositions as described herein is from about 0.05% w/w to about 2% w/w, about 0.05% w/w to about 1.5% w/w, about 0.05% w/w to about 1.4% w/w, about 0.05% w/w to about 1.3% w/w, about 0.05% w/w to about 1.2% w/w, about 0.05% w/w to about 1.1% w/w, about 0.05% w/w to about 1.0% w/w, about 0.05% w/w to about 0.8% w/w, about 0.05% w/w to about 0.6% w/w, about 0.05% w/w to about 0.5% w/w, about 0.05% w/w to about 0.4% w/w, about 0.05% w/w to about 0.3% w/w, about 0.05% w/w to about 0.2% w/w, about 0.05% w/w to about 0.1% w/w, about 0.05% w/w to about 0.07% w/w, about 0.07% w/w to about 1.5% w/w, about 0.07% w/w to about 1.4% w/w, about 0.07% w/w to about 1.3% w/w, about 0.07% w/w to about 1.2% w/w, about 0.07% w/w to about 1.1% w/w, about 0.07% w/w to about 1.0% w/w, about 0.07% w/w to about 0.8% w/w, about 0.07% w/w to about 0.6% w/w, about 0.07% w/w to about 0.5% w/w, about 0.07% w/w to about 0.4% w/w, about 0.07% w/w to about 0.3% w/w, about 0.07% w/w to about 0.2% w/w, about 0.07% w/w to about 0.1% w/w, about 0.1% w/w to about 1.5% w/w, about 0.1% w/w to about 1.4% w/w, about 0.1% w/w to about 1.3% w/w, about 0.1% w/w to about 1.2% w/w, about 0.1% w/w to about 1.1% w/w, about 0.1% w/w to about 1.0% w/w, about 0.1% w/w to about 0.8% w/w, about 0.1% w/w to about 0.5% w/w, about 0.1% w/w to about 0.4% w/w, about 0.1% w/w to about 0.3% w/w, about 0.1% w/w to about 0.2% w/w, about 0.2% w/w to about 1.5% w/w, about 0.2% w/w to about 1.4% w/w, about 0.2% w/w to about 1.3% w/w, about 0.2% w/w to about 1.2% w/w, about 0.2% w/w to about 1.1% w/w, about 0.2% w/w to about 1.0% w/w, about 0.2% w/w to about 0.8% w/w, about 0.2% w/w to about 0.6% w/w, about 0.2% w/w to about 0.5% w/w, about 0.2% w/w to about 0.4% w/w, about 0.2% w/w to about 0.3% w/w, about 0.3% w/w to about 1.5% w/w, about 0.3% w/w to about 1.4% w/w, about 0.3% w/w to about 1.3% w/w, about 0.3% w/w to about 1.2% w/w, about 0.3% w/w to about 1.1% w/w, about 0.3% w/w to about 1.0% w/w, about 0.3% w/w to about 0.8% w/w, about 0.3% w/w to about 0.6% w/w, about 0.3% w/w to about 0.5% w/w, about 0.3% w/w to about 0.4% w/w, about 0.4% w/w to about 1.5% w/w, about 0.4% w/w to about 1.4% w/w, about 0.4% w/w to about 1.3% w/w, about 0.4% w/w to about 1.2% w/w, about 0.4% w/w to about 1.1% w/w, about 0.4% w/w to about 1.0% w/w, about 0.4% w/w to about 0.8% w/w, about 0.4% w/w to about 0.6% w/w, about 0.4% w/w to about 0.5% w/w, about 0.5% w/w to about 1.5% w/w, about 0.5% w/w to about 1.4% w/w, about 0.5% w/w to about 1.3% w/w, about 0.5% w/w to about 1.2% w/w, about 0.5% w/w to about 1.1% w/w, about 0.5% w/w to about 1.0% w/w, about 0.5% w/w to about 0.8% w/w, about 0.5% w/w to about 0.6% w/w, about 0.6% w/w to about 1.5% w/w, about 0.6% w/w to about 1.4% w/w, about 0.6% w/w to about 1.3% w/w, about 0.6% w/w to about 1.2% w/w, about 0.6% w/w to about 1.1% w/w, about 0.6% w/w to about 1.0% w/w, about 0.6% w/w to about 0.8% w/w, about 0.8% w/w to about 1.5% w/w, about 0.8% w/w to about 1.4% w/w, about 0.8% w/w to about 1.3% w/w, about 0.8% w/w to about 1.2% w/w, about 0.8% w/w to about 1.1% w/w, about 0.8% w/w to about 1.0% w/w, about 1.0% w/w to about 1.5% w/w, about 1.0% w/w to about 1.4% w/w, about 1.0% w/w to about 1.3% w/w, about 1.0% w/w to about 1.2% w/w, about 1.0% w/w to about 1.1% w/w, about 1.1% w/w to about 1.5% w/w, about 1.1% w/w to about 1.4% w/w, about 1.1% w/w to about 1.3% w/w, about 1.1% w/w to about 1.2% w/w, about 1.2% w/w to about 1.5% w/w, about 1.2% w/w to about 1.4% w/w, about 1.2% w/w to about 1.3% w/w, about 1.3% w/w to about 1.5% w/w, about 1.3% w/w to about 1.4% w/w, or about 1.4% w/w to about 1.5% w/w. In some embodiments, the amount of unsubstituted beta-cyclodextrin in the hydroxypropyl-beta-cyclodextrin compositions as described herein is from about 0.05% w/w to about 2% w/w. In some embodiments, the amount of unsubstituted beta-cyclodextrin in the hydroxypropyl-beta-cyclodextrin compositions as described herein is from about 0.1% w/w to about 0.2% w/w.

In certain embodiments, the hydroxypropyl-beta-cyclodextrin compositions of the present invention may comprise an impurity resulting from the chemical synthesis of the hydroxypropyl-beta-cyclodextrin species. In some embodiments, the impurity is propylene glycol.

In certain embodiments, the hydroxypropyl-beta-cyclodextrin compositions as described herein comprise less than about 2.0%, less than about 2.1% w/w, less than about 2.2% w/w, less than about 2.3% w/w, less than about 2.4% w/w, less than about 2.5% w/w, less than about 2.6% w/w, less than about 2.7% w/w, less than about 2.8% w/w, less than about 2.9% w/w, or less than about 3% w/w propylene glycol. In some embodiments, the hydroxypropyl-beta-cyclodextrin compositions as described herein comprise less than about 2.5% w/w propylene glycol.

In certain embodiments, the hydroxypropyl-beta-cyclodextrin compositions as described herein comprise 2.0% or less, 2.1% w/w or less, 2.2% w/w or less, 2.3% w/w or less, 2.4% w/w or less, 2.5% w/w or less, 2.6% w/w or less, 2.7% w/w or less, 2.8% w/w or less, 2.9% w/w or less, or 3% w/w or less of propylene glycol. In some embodiments, the hydroxypropyl-beta-cyclodextrin compositions as described herein comprise 2.5% w/w or less of propylene glycol.

In certain embodiments, the amount of propylene glycol in the hydroxypropyl-beta-cyclodextrin compositions as described herein is from about 2.0% w/w to about 3.0% w/w, about 2.0% w/w to about 2.9% w/w, about 2.0% w/w to about 2.8% w/w, about 2.0% w/w to about 2.7% w/w, about 2.0% w/w to about 2.6% w/w, about 2.0% w/w to about 2.5% w/w, about 2.0% w/w to about 2.4% w/w, about 2.0% w/w to about 2.3% w/w, about 2.0% w/w to about 2.2% w/w, about 2.0% w/w to about 2.1% w/w, about 2.1% w/w to about 3.0% w/w, about 2.1% w/w to about 2.9% w/w, about 2.1% w/w to about 2.8% w/w, about 2.1% w/w to about 2.7% w/w, about 2.1% w/w to about 2.6% w/w, about 2.1% w/w to about 2.5% w/w, about 2.1% w/w to about 2.4% w/w, about 2.1% w/w to about 2.3% w/w, about 2.1% w/w to about 2.2% w/w, about 2.2% w/w to about 3.0% w/w, about 2.2% w/w to about 2.9% w/w, about 2.2% w/w to about 2.8% w/w, about 2.2% w/w to about 2.6% w/w, about 2.2% w/w to about 2.5% w/w, about 2.2% w/w to about 2.4% w/w, about 2.2% w/w to about 2.3% w/w, about 2.3% w/w to about 3.0% w/w, about 2.3% w/w to about 2.9% w/w, about 2.3% w/w to about 2.8% w/w, about 2.3% w/w to about 2.7% w/w, about 2.3% w/w to about 2.6% w/w, about 2.3% w/w to about 2.5% w/w, about 2.3% w/w to about 2.4% w/w, about 2.4% w/w to about 3.0% w/w, about 2.4% w/w to about 2.9% w/w, about 2.4% w/w to about 2.8% w/w, about 2.4% w/w to about 2.7% w/w, about 2.4% w/w to about 2.6% w/w, about 2.4% w/w to about 2.5% w/w, about 2.5% w/w to about 3.0% w/w, about 2.5% w/w to about 2.9% w/w, about 2.5% w/w to about 2.8% w/w, about 2.5% w/w to about 2.7% w/w, about 2.5% w/w to about 2.6% w/w, about 2.6% w/w to about 3.0% w/w, about 2.6% w/w to about 2.9% w/w, about 2.6% w/w to about 2.8% w/w, about 2.6% w/w to about 2.7% w/w, about 2.7% w/w to about 3.0% w/w, about 2.7% w/w to about 2.9% w/w, about 2.7% w/w to about 2.8% w/w, about 2.8% w/w to about 3.0% w/w, about 2.8% w/w to about 2.9% w/w, or about 2.9% w/w to about 3.0% w/w. In some embodiments, the amount of propylene glycol in the hydroxypropyl-beta-cyclodextrin compositions as described herein is from about 2.0% w/w to about 3.0% w/w.

In certain embodiments, the hydroxypropyl-beta-cyclodextrin composition comprises a mixture of two or more hydroxypropyl-beta-cyclodextrin species, wherein each of the two or more hydroxypropyl-beta-cyclodextrin species has a different degree of hydroxypropylation of the beta-cyclodextrin ring, and wherein the hydroxypropyl-beta-cyclodextrin composition comprises 0.15% w/w or less of unsubstituted beta-cyclodextrin.

In certain embodiments, the hydroxypropyl-beta-cyclodextrin composition comprises a mixture of two or more hydroxypropyl-beta-cyclodextrin species, wherein each of the two or more hydroxypropyl-beta-cyclodextrin species has a different degree of hydroxypropylation of the beta-cyclodextrin ring, wherein the mixture of two or more hydroxypropyl-beta-cyclodextrin species has a molar substitution value from about 0.59 to about 0.73, and wherein the hydroxypropyl-beta-cyclodextrin composition comprises 2.5% w/w or less of propylene glycol and 0.15% w/w or less of unsubstituted beta-cyclodextrin.

In certain embodiments, the hydroxypropyl-beta-cyclodextrin composition comprises a 5% (w/v), 10% (w/v), 15% (w/v), 20% (w/v), 25% (w/v), 30% (w/v), 35% (w/v) or 40% (w/v) solution of one or more hydroxypropyl-beta-cyclodextrin species. In some embodiments, the hydroxypropyl-beta-cyclodextrin composition comprises a 25% (w/v) solution of one or more hydroxypropyl-beta-cyclodextrin species. In some embodiments, the 25% (w/v) solution of one or more hydroxypropyl-beta-cyclodextrin species is a 25% (w/v) aqueous solution of one or more hydroxypropyl-beta-cyclodextrin species.

In certain embodiments, the hydroxypropyl-beta-cyclodextrin composition comprises the Trappsol® Cyclo™ hydroxypropyl-beta-cyclodextrin composition, available from CTD Holdings, Inc.

Treatment of Alzheimer's Disease with Hydroxypropyl-Beta-Cyclodextrins

Effect of Cholesterol on Alzheimer's Disease

Alzheimer's disease (AD) neuropathology may be characterized by 1) amyloid-beta (Aβ) containing plaques and 2) neurofibrillary tangles composed of neurofilaments and hyperphosphorylated tau protein. While the exact role of the Aβ plaques and tau tangles play in AD is unknown, it is believed that they play a critical role in blocking communication among nerve cells and disrupting the critical processes cells require in order to survive. Moreover, studies have demonstrated that Aβ is neurotoxic and there is evidence to suggest that it appears to be responsible for initiating the memory loss associated with AD.

Cholesterol is considered to be essential for cell structure, function and signaling. Approximately twenty-three percent of all cholesterol in the body is located within the brain; with neurons and astrocytes containing the largest amounts. Cholesterol is not uniformly distributed: as variations exist both within each particular membrane and across different membranes of the same cell. Within each membrane, cholesterol is concentrated at nano/micro domains termed 'lipid rafts.' In neurons, these rafts are highly dynamic, thought to be a result of their high metabolic demands and requirement for plasticity and re-modelling throughout life. Rafts have also been detected at neuronal synapses, where they contribute to pre- and post-synaptic function. Within a single neuron, the relative distribution of cholesterol also varies across intracellular membranes. The vast majority (>90%) of cholesterol is located within the plasma membrane. Once across the plasma membrane, most cholesterol is shuttled to endosomes/lysosomes and then on to certain organelles for processing, where it may be incorporated into other organelle membranes (i.e. mitochondria, lysosome, endoplasmic reticulum) or esterified and stored in the form of cytosolic lipid droplets.

Subjects suffering from AD often suffer from cholesterol imbalances and existing studies suggest that these imbalances may be responsible for Aβ and tau accumulation. Furthermore, neurons, due to their high metabolic demands, may experience an increased level of oxidative stress. Oxidative stress has been linked to abnormal cholesterol accumulation and processing. Studies have shown that that young or juvenile neurons have lower membrane cholesterol levels than mature neurons. Furthermore, cadaver studies of AD patients have also shown that levels of cellular cholesterol are significantly increased in the membranes within vulnerable brain regions, but not non-vulnerable brain regions. The amount of cholesterol in these membranes has also been found to be greater in patients with more severe cognitive symptoms than in patients with mild impairment.

Cells of the brain are largely cut off from blood cholesterol supply because the blood-brain barrier prevents entry of cholesterol rich lipoproteins. Therefore, most CNS cholesterol is made locally. On the other hand, there is a constant efflux of cholesterol from the brain through neuron specific enzyme Cytochrome 46A1. This enzyme hydroxylates cholesterol to 24S-hydroxycholesterol (24-OHC), which crosses the blood brain barrier, to enter circulation. Altered CYP46A1 expression has been associated with several neurodegenerative diseases and changes in cognition. A second mechanism of efflux is HDL, which can cross the blood-brain barrier, and transports cholesterol out of the brain, to the plasma and then on to the liver for eventual removal. Low and/or dysfunctional HDL particles are known risk factors for developing AD. Finally, apolipoprotein E (APOE) isoform type ε4, which is a form of LDL and regulates brain cholesterol metabolism and transport may be the strongest identified genetic risk factor for the development of AD.

There is an established link between Aβ and cholesterol, as both the generation and clearance of Aβ are regulated by cholesterol. Increasing cholesterol content, particularly in domains such as the plasma membrane, can result in increased Aβ levels, as has been shown in both cell culture and most animal models of AD. Tau toxicity may also depend on cellular cholesterol levels. High cholesterol diets have been shown to increase tau hyper phosphorylation. Studies have shown that as cholesterol concentration increases, so does the susceptibility of neurons to Aβ-dependent calpain activation. Calpain activation is known to cleave tau and generate toxic fragments. These cleaved tau forms can induce neuronal death, synapse loss, and/or behavioral deficits. Young neurons which have measurably less cholesterol than aged neurons, also contain less phosphorylated tau (p-tau).

Treating AD with Hydroxypropyl-Beta-Cyclodextrins

HPβCD is known to form complexes with cholesterol and has been routinely used to modulate the cellular cholesterol content in cell culture systems. In some embodiments, cellular cholesterol content may be manipulated by modifying the cyclodextrin:cholesterol molar ratio. In some embodiments, modification of the cyclodextrin:cholesterol molar ratio results in cholesterol depletion. In some embodiments, modification of the cyclodextrin:cholesterol molar ratio results in cholesterol enrichment. At high cellular concentrations (10-100 mM), HPβCD may serve as a cholesterol sink and may be used to extract and trap cholesterol. However, at low concentrations (<1-3 mM), HPβCD may also act as a cholesterol shuttle and transport cholesterol between membranes.

In one aspect, provided herein is a method of treating Alzheimer's disease in a subject suffering from Alzheimer's disease comprising administering an effective amount of a hydroxypropyl-beta-cyclodextrin composition disclosed herein. In some embodiments, the subject is a human.

In another aspect, provided herein is a method of treating Alzheimer's disease in a human patient suffering from Alzheimer's disease comprising administering an effective amount of a hydroxypropyl-beta-cyclodextrin composition.

In certain embodiments, the patient has progression of the Alzheimer's disease after previous administration of another therapy. In some embodiments, the previous administration of another therapy is a therapy for Alzheimer's disease. In some embodiments, the therapy for Alzheimer's disease is selected from the group comprising ABBV-8E12 (anti-tau antibody), AC-1204 (glucose stimulant), ACI-24 (anti-Abeta vaccine), ACI-35 (anti-pTau vaccine), aducanumab (BIIB037) (amyloid beta mAb), AGB101 (levetiracetam low-dose), ALZ-801 (amyloid beta-protein inhibitor), ALZT-OP1 (amyloid beta-protein inhibitor/inflammation mediator inhibitor), AMG520/CNP520 (BACE1 protein inhibitor), ANAVEX™ 2-73 (M1 muscarinic receptor agonist/intracellular sigma 1 receptor agonist), AstroStem (mesenchymal stem cell therapy, AUS-131 (nonhormonal estrogen receptor agonist), AVN-101 (serotonin 6 receptor antagonist), AVN-322 (serotonin 6 receptor antagonist), AVP-786 (dextromethorphan analogue/ultra-low dose quinidine), AXS-05 (bupropion/dextromethorphan), azeliragon (TTP488) (RAGE antagonist), BAN2401 (anti-amyloid beta mAb), Bexarotene (RXR-selective retinoid analogue), BI 409306 (PDE9A inhibitor), BIIB076 (anti-tau antibody), BIIB092 (anti-extracellular tau antibody), BNC375 (positive allosteric modulator), BPN14770 (type 4 cyclic nucleotide phosphodiesterase inhibitor), bryostatin 1 (protein kinase C stimulant), CAD106 (amilomotide) (VLP immunotherapy vaccine), Corplex Donepezil (donepezil transdermal patch, Corplex Memantine (memantine transdermal patch, CPC-201 (donepezil/solifenacin combination), CPC-212 (next-generation acetylcholinesterase inhibitor), CPC-250 (next-generation acetylcholine-sterase inhibitor), Crenezumab (anti-amyloid beta antibody), CSP-1103 (amyloid beta-protein inhibitor), CSTC1 (BAC), CT1812 (amyloid beta oligomer receptor antagonist), E2027 (PDE9 inhibitor), E2609 (BACE1 protein inhibitor), EVT302 (MAO-B inhibitor), gantenerumab (amyloid beta-protein inhibitor), GC021109 (purinoceptor P2Y6 agonist), HSRx-888 (donepezil/food-based compound), immune globulin/albumin, INP-102 intranasal, intepirdine (RVT-101) (serotonin 6 receptor antagonist), IONIS-MAPTRx (tau-targeting protein), JNJ-54861911 (BACE inhibitor), JOT106 (oral capsule of trans-resveratrol), KPAX002-2 (proprietary version of methylphenidate), lanabecestat (BACE inhibitor), LM11A-31 (p75 neutrophin receptor), LMTX (tau protein aggregation inhibitor/TDP-43 aggregation inhibitor), LY3002813 (N3pG-amyloid beta antibody), LY3202626 (BACE inhibitor), LY3303560 (tau antibody), M1 agonist (selective M1 receptor agonist), MEDI1814 (anti-amyloid beta 42 mAb), mesenchymal stem cell therapy, MP-101 (mGluR2/mGluR3 agonist), MSDC-0160 (mTOT modulator), NBXT-001+Nobilis™ inhalation device (NMDA receptor antagonist), neflamapimod (VX-745) (p38 mitogen-activated protein kinase inhibitor), NGP 555 (gamma secretase complex modulator), nilvadipine soluble amyloid reducing/clearing agent), NPT088 (GAIM Ig fusion targeting amyloid-ß, tau, a-synuclein), Nuplazid® pimavanserin, PF-05251749 (casein kinase 1 delta/epsilon), PF-06648671 (gamma secretase complex modulator), PF-06751979 (enzyme inhibitor), pioglitazone (low-dose) (PPARγ agonist), piromelatine (melatonin agonist), Posiphen® R-phenserine, Rexulti® brexpiprazole, RG6100 (tau protein inhibitor), RVT-103+RVT-104 (QAAM+cholinesterase inhibitor), SAR228810 (anti-protofibrillar AB mAb), selective BACE 1 inhibitor, solanezumab (amyloid beta protein inhibitor), SUVN-502 (serotonin 6 receptor antagonist), SUVN-D4010 (serotonin 4 receptor agonist), SUVN-G3031 (histamine H3 receptor antagonist), T-817MA (amyloid beta-protein inhibitor), T3D-959 (PPAR-delta/gamma agonist), TAK-071 (muscarinic M1 receptor modulator), TPI 287 (next-generation taxane), UB-311 (anti-amyloid endobody vaccine), UE-2343 (11ß-HSD1 inhibitor), verubecestat (MK-8931) (BACE1 protein inhibitor), or combinations thereof.

In certain embodiments, the human patient is at least 40 years old, at least 45 years old, at least 50 years old, at least 55 years old, at least 60 years old, at least 65 years old, at least 70 years old, at least 75 years old, at least 80 years old, at least 85 years old, or at least 90 years old. In some embodiments, the human patient is at least 50 years old. In some embodiments, the human patient is at least 60 years old. In some embodiments, the human patient is at least 65 years old. In some embodiments, the human patient is at least 70 years old. In some embodiments, the human patient is at least 80 years old.

In certain embodiments, the amount of the hydroxypropyl-beta-cyclodextrin composition to be administered to the human patient is determined by the patient's body weight. In some embodiments, the dose amount to be administered to the patient is given in mg/kg patient body weight.

In certain embodiments, the method comprises administering the hydroxypropyl-beta-cyclodextrin composition to the human patient in a dose amount of about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 150 mg/kg, about 200 mg/kg, about 250 mg/kg, about 300 mg/kg, about 350 mg/kg, about 400 mg/kg, about 450 mg/kg, about 500 mg/kg, about 600 mg/kg, about 700 mg/kg, about 800 mg/kg, about 900 mg/kg, about 1000 mg/kg, about 1100 mg/kg, about 1200 mg/kg, about 1300 mg/kg, about 1400 mg/kg, about 1500 mg/kg, about 1600 mg/kg, about 1700 mg/kg, about 1800 mg/kg, about 1900 mg/kg, about 2000 mg/kg, about 2100 mg/kg, about 2200 mg/kg, about 2300 mg/kg, about 2400 mg/kg, about 2500 mg/kg, about 3000 mg/kg, about 3500 mg/kg, about 4000 mg/kg, about 4500 mg/kg, or about 5000 mg/kg. In some embodiments, the method comprises administering the hydroxypropyl-beta-cyclodextrin composition to the human patient in a dose amount of about 500 mg/kg. In some embodiments, the method comprises administering the hydroxypropyl-beta-cyclodextrin composition to the human patient in a dose amount of about 750 mg/kg. In some embodiments, the method comprises administering the hydroxypropyl-beta-cyclodextrin composition to the human patient in a dose amount of about 1000 mg/kg. In some embodiments, the method comprises administering the hydroxypropyl-beta-cyclodextrin composition to the human patient in a dose amount of about 1500 mg/kg.

In some embodiments, the method comprises administering the hydroxypropyl-beta-cyclodextrin composition to the human patient in a dose amount from about 100 mg/kg to about 3000 mg/kg, about 500 mg/kg to about 3000 mg/kg, about 1000 mg/kg to about 3000 mg/kg, about 1500 mg/kg to about 3000 mg/kg, about 2000 mg/kg to about 3000 mg/kg, about 2500 mg/kg to about 3000 mg/kg, about 100 mg/kg to about 2500 mg/kg, about 100 mg/kg to about 2000 mg/kg, about 100 mg/kg to about 1500 mg/kg, about 100 mg/kg to about 1000 mg/kg, about 100 mg/kg to about 500 mg/kg, about 500 mg/kg to about 2500 mg/kg, about 500 mg/kg to about 2000 mg/kg, about 500 mg/kg to about 1500 mg/kg, about 500 mg/kg to about 1000 mg/kg, about 1000 mg/kg to about 2500 mg/kg, about 1000 mg/kg to about 2000 mg/kg, about 1000 mg/kg to about 1500 mg/kg, about 1500 mg/kg to about 2500 mg/kg, about 1500 mg/kg to about 2000 mg/kg, or about 2000 mg/kg to about 2500 mg/kg. In some embodiments, the method comprises administering the hydroxypropyl-beta-cyclodextrin composition to the human patient in a dose amount from about 500 mg/kg to about 1500 mg/kg. In some embodiments, the method comprises administering the hydroxypropyl-beta-cyclodextrin composition to the human patient in a dose amount from about 500 mg/kg to about 1000 mg/kg. In some embodiments, the method comprises administering the hydroxypropyl-beta-cyclodextrin composition to the human patient in a dose amount from about 750 mg/kg to about 1000 mg/kg.

In certain embodiments, the method comprises administering the hydroxypropyl-beta-cyclodextrin to the human patient in a dose directed to the central nervous system (CNS) in an amount of about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, or about 750 mg.

In certain embodiments, the method comprises administering the hydroxypropyl-beta-cyclodextrin to the human patient in a dose directed to the CNS in an amount of from about 100 mg to about 750 mg, from about 150 mg to about 750 mg, from about 300 mg to about 750 mg, from about 450 mg to about 750 mg, from about 600 mg to about 750 mg, from about 100 mg to about 600 mg, from about 150 mg to about 600 mg, from about 300 mg to about 600 mg, from about 450 mg to about 600 mg, from about 100 mg to about 450 mg, from about 150 mg to about 450 mg, from about 300 mg to about 450 mg, from about 100 mg to about 300 mg, from about 150 mg to about 300 mg, or from about 100 mg to about 150 mg. In some embodiments, the method comprises administering the hydroxypropyl-beta-cyclodextrin to the human patient in a dose directed to the CNS in an amount of about 100 mg to about 750 mg.

In certain embodiments, the hydroxypropyl-beta-cyclodextrin composition is administered once a month, twice a month, weekly, or daily. In some embodiments, the hydroxypropyl-beta-cyclodextrin composition is administered once a month.

In certain embodiments, the hydroxypropyl-beta-cyclodextrin composition is administered once a month for a period of at least 1 month, at least 2 months, at least 3 months, at least 4 months, at least 5 months, at least 6 months, at least 7 months, at least 8 months, at least 9 months, at least 10 months, at least 11 months, at least 12 months, at least 1 year, at least 2 years, at least 3 years, at least 4 years, at least 5 years, at least 6 years, at least 7 years, at least 8 years, at least 9 years, at least 10 years, at least 15 years, at least 20 years or at least 25 years. In some embodiments, the hydroxypropyl-beta-cyclodextrin composition is administered once a month for a period of at least 12 months. In some embodiments, the hydroxypropyl-beta-cyclodextrin composition is administered once a month for up to the duration of the lifespan of the human patient.

In certain embodiments, the method further comprises administering the hydroxypropyl-beta-cyclodextrin composition in a monthly dose amount selected from the group consisting of 50 mg/kg, 100 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1,000 mg/kg, 1,250 mg/kg, 1,500 mg/kg, 2,000 mg/kg, 2,500 mg/kg, 3,000 mg/kg, 3,500 mg/kg, 4,000 mg/kg, 4,500 mg/kg, or 5,000 mg/kg. In some embodiments, the method further comprises administering the hydroxypropyl-beta-cyclodextrin composition in a monthly dose amount selected from the group consisting of 500 mg/kg, 750 mg/kg, 1,000 mg/kg, 1,500 mg/kg, 2,000 mg/kg, or 2,500 mg/kg. In some embodiments, the method further comprises administering the hydroxypropyl-beta-cyclodextrin composition in a monthly dose amount of 500 mg/kg. In some embodiments, the method further comprises administering the hydroxypropyl-beta-cyclodextrin composition in a monthly dose amount of 750 mg/kg. In some embodiments, the method further comprises administering the hydroxypropyl-beta-cyclodextrin composition in a monthly dose amount of 1000 mg/kg. In some embodiments, the method further comprises administering the hydroxypropyl-beta-cyclodextrin composition in a monthly dose amount of 1500 mg/kg.

In certain embodiments, the method further comprises administering the hydroxypropyl-beta-cyclodextrin composition in a monthly dose amount directed to the CNS selected from the group consisting of about 100 mg, about 150 mg, about 200 mg, about 250 mg, about 300 mg, about 350 mg, about 400 mg, about 450 mg, about 500 mg, about 550 mg, about 600 mg, about 650 mg, about 700 mg, or about 750 mg.

In certain embodiments, the method further comprises administering the hydroxypropyl-beta-cyclodextrin composition in a monthly escalating dose regimen, until a maximum tolerated dose is determined. In some embodiments, having determined the maximum tolerated dose, the maximum tolerated dose of the hydroxypropyl-beta-cyclodextrin composition is administered to the patient once a month for a period of 1 month, 2 months, 3 months, 4 months, 5 months, 6 months, 7 months, 8 months, 9 months, 10 months, 11 months, 12 months, 1 year, 2 years, 3 years, 4 years, 5 years, 6 years, 7 years, 8 years, 9 years, 10 years, 15 years, 20 years or 25 years. In some embodiments, having determined the maximum tolerated dose, the maximum tolerated dose of the hydroxypropyl-beta-cyclodextrin composition is administered to the patient once a month up to the duration of the lifespan of the human patient.

In certain embodiments, the method further comprises administering the hydroxypropyl-beta-cyclodextrin composition in a monthly escalating dose regimen until a maximum tolerated dose is determined, and subsequently administering the maximum tolerated dose. In some embodiments, the method further comprises administering the hydroxypropyl-beta-cyclodextrin composition in a monthly escalating dose regimen in an amount of 500 mg/kg during month one and month 2, 1,000 mg/kg during months 3 and 4, 1,500 mg/kg during months 5 and 6, 2,000 mg/kg during months 7 and 8 and 2,500 mg/kg during months 9 and 10, until a maximum tolerated dose is determined, and subsequently administering the maximum tolerated dose.

In certain embodiments, the method further comprises administering the maximum tolerated dose of the hydroxypropyl-beta-cyclodextrin composition monthly for at least 6 months, at least 7 months, at least 8 months, at least 9 months, at least 10 months, at least 11 months, at least 12 months, at least 1 year, at least 2 years, at least 3 years, at least 4 years, at least 5 years, at least 6 years, at least 7 years, at least 8 years, at least 9 years, at least 10 years, at least 15 years, at least 20 years or at least 25 years. In some embodiments, the method further comprises administering the maximum tolerated dose of the hydroxypropyl-beta-cyclodextrin composition monthly for up to the duration of the lifespan of the human patient. In some embodiments, the method further comprises administering the maximum tolerated dose of the hydroxypropyl-beta-cyclodextrin composition monthly for at least 12 months.

In certain embodiments, the method comprises administering a hydroxypropyl-beta-cyclodextrin composition as described herein to the human patient by a route of administration selected from the group consisting of intracavitary, intradermal, intramuscular, intrathecal, intravenous, subcutaneous, intracerebroventricular and any combination thereof.

In some embodiments, the method further comprises administering a second therapeutic agent selected from the group consisting of donepezil, rivastigmine, galantamine, memantine, verubecestat, solanezumab, bapineuzumab, aducanumab, tideglusib, epothilone D and ABBV-8E12 or other therapeutic agent for the treatment of Alzheimer's disease currently in development.

In certain embodiments, the method further comprises administering a second therapeutic agent selected from the group consisting of a cholinesterase inhibitor, an NMDA receptor antagonist, a humanized antibody which targets tau protein, a humanized antibody which targets amyloid beta protein, and a BACE inhibitor.

In certain embodiments, the method further comprises administering a second therapeutic agent selected from the group consisting of Aricept®, Namenda®, donepezil, memantine, Excelon, Namenda® XR, galantamine, Aricept® ODT, rivastigmine, vitamin e, Razadyne® ER, donepezil/memantine, Razadyne®, Namzaric®, Alpha E®, Hydergine®, ergoloid mesylates, Aqua-E®, Aqua® Gem-E, etanercept, Reminyl®, Vita-Plus E natural, Aquasol® E, Aquavite®-E and E-400 clear.

In certain embodiments, the method further comprises administering a second therapeutic agent, wherein the second therapeutic agent is selected from the group consisting of ABBV-8E12 (anti-tau antibody), AC-1204 (glucose stimulant), ACI-24 (anti-Abeta vaccine), ACI-35 (anti-pTau vaccine), aducanumab (BIIB037) (amyloid beta mAb), AGB101 (levetiracetam low-dose), ALZ-801 (amyloid beta-protein inhibitor), ALZT-OP1 (amyloid beta-protein inhibitor/inflammation mediator inhibitor), AMG520/CNP520 (BACE1 protein inhibitor), ANAVEX™ 2-73 (M1 muscarinic receptor agonist/intracellular sigma 1 receptor agonist), AstroStem (mesenchymal stem cell therapy, AUS-131 (nonhormonal estrogen receptor agonist), AVN-101 (serotonin 6 receptor antagonist), AVN-322 (serotonin 6 receptor antagonist), AVP-786 (dextromethorphan analogue/ultra-low dose quinidine), AXS-05 (bupropion/dextromethorphan), azeliragon (TTP488) (RAGE antagonist), BAN2401 (anti-amyloid beta mAb), Bexarotene (RXR-selective retinoid analogue), BI 409306 (PDE9A inhibitor), BIIB076 (anti-tau antibody), BIIB092 (anti-extracellular tau antibody), BNC375 (positive allosteric modulator), BPN14770 (type 4 cyclic nucleotide phosphodiesterase inhibitor), bryostatin 1 (protein kinase C stimulant), CAD106 (amilomotide) (VLP immunotherapy vaccine), Corplex Donepezil (donepezil transdermal patch, Corplex Memantine (memantine transdermal patch, CPC-201 (donepezil/solifenacin combination), CPC-212 (next-generation acetylcholinesterase inhibitor), CPC-250 (next-generation acetylcholine-sterase inhibitor), Crenezumab (anti-amyloid beta antibody), CSP-1103 (amyloid beta-protein inhibitor), CSTC1 (BAC), CT1812 (amyloid beta oligomer receptor antagonist), E2027 (PDE9 inhibitor), E2609 (BACE1 protein inhibitor), EVT302 (MAO-B inhibitor), gantenerumab (amyloid beta-protein inhibitor), GC021109 (purinoceptor P2Y6 agonist), HSRx-888 (donepezil/food-based compound), immune globulin/albumin, INP-102 intranasal, intepirdine (RVT-101) (serotonin 6 receptor antagonist), IONIS-MAPTRx (tau-targeting protein), JNJ-54861911 (BACE inhibitor), JOT106 (oral capsule of trans-resveratrol), KPAX002-2 (proprietary version of methylphenidate), lanabecestat (BACE inhibitor), LM11A-31 (p75 neutrophin receptor), LMTX (tau protein aggregation inhibitor/TDP-43 aggregation inhibitor), LY3002813 (N3pG-amyloid beta antibody), LY3202626 (BACE inhibitor), LY3303560 (tau antibody), M1 agonist (selective M1 receptor agonist), MEDI1814 (anti-amyloid beta 42 mAb), mesenchymal stem cell therapy, MP-101 (mGluR2/mGluR3 agonist), MSDC-0160 (mTOT modulator), NBXT-001+Nobilis™ inhalation device (NMDA receptor antagonist), neflamapimod (VX-745) (p38 mitogen-activated protein kinase inhibitor), NGP 555 (gamma secretase complex modulator), nilvadipine soluble amyloid reducing/clearing agent), NPT088 (GAIM Ig fusion targeting amyloid-ß, tau, a-synuclein), Nuplazid® pimavanserin, PF-05251749 (casein kinase 1 delta/epsilon), PF-06648671 (gamma secretase complex modulator), PF-06751979 (enzyme inhibitor), pioglitazone (low-dose) (PPARγ agonist), piromelatine (melatonin agonist), Posiphen® R-phenserine, Rexulti® brexpiprazole, RG6100 (tau protein inhibitor), RVT-103+RVT-104 (QAAM+cholinesterase inhibitor), SAR228810 (anti-protofibrillar Aβ mAb), selective BACE 1 inhibitor, solanezumab (amyloid beta protein inhibitor), SUVN-502 (serotonin 6 receptor antagonist), SUVN-D4010 (serotonin 4 receptor agonist), SUVN-G3031 (histamine H3 receptor antagonist), T-817MA (amyloid beta-protein inhibitor), T3D-959 (PPAR-delta/gamma agonist), TAK-071 (muscarinic M1 receptor modulator), TPI 287 (next-generation taxane), UB-311 (anti-amyloid endobody vaccine), UE-2343 (11ß-HSD1 inhibitor), verubecestat (MK-8931) (BACE1 protein inhibitor), or combinations thereof.

In certain embodiments, the method further comprises administering a second therapeutic agent, wherein the second therapeutic agent is selected from any therapeutic agent set forth in Table 1.

TABLE 1

Therapeutic agents for the treatment of Alzheimer's disease.

| | | | |
|---|---|---|---|
| ABBV-8E12 (anti-tau antibody) | AC-1204 (glucose stimulant) | ACI-24 (anti-Abeta vaccine) | ACI-35 (anti-pTau vaccine) |
| aducanumab (BIIB037) (amyloid beta mAb) | AGB101 (levetiracetam low-dose) | ALZ-801 (amyloid beta-protein inhibitor) | ALZT-OP1 (amyloid beta-protein inhibitor/inflammation mediator inhibitor) |
| AMG520/CNP520 (BACE1 protein inhibitor) | ANAVEX ™ 2-73 (M1 muscarinic receptor agonist/intracellular sigma 1 receptor agonist) | AstroStem (mesenchymal stem cell therapy | AUS-131 (nonhormonal estrogen receptor agonist) |
| AVN-101 (serotonin 6 receptor antagonist) | AVN-322 (serotonin 6 receptor antagonist) | AVP-786 (dextromethorphan analogue/ultra- low dose quinidine) | AXS-05 (bupropion/dextromethorphan) |
| azeliragon (TTP488) (RAGE antagonist) | BAN2401 (anti-amyloid beta mAb) | Bexarotene (RXR-selective retinoid analogue) | BI 409306 (PDE9A inhibitor) |
| BIIB076 (anti-tau antibody) | BIIB092 (anti-extracellular tau antibody) | BNC375 (positive allosteric modulator) | BPN14770 (type 4 cyclic nucleotide phosphodiesterase inhibitor) |
| bryostatin 1 (protein kinase C stimulant) | CAD106 (amilomotide) (VLP immunotherapy vaccine) | Corplex Donepezil (donepezil transdermal patch | Corplex Memantine (memantine transdermal patch |

TABLE 1-continued

Therapeutic agents for the treatment of Alzheimer's disease.

| | | | |
|---|---|---|---|
| CPC-201 (donepezil/solifenacin combination) | CPC-212 (next-generation acetylcholinesterase inhibitor) | CPC-250 (next-generation acetylcholine-sterase inhibitor) | Crenezumab (anti-amyloid beta antibody) |
| CSP-1103 (amyloid beta-protein inhibitor) | CSTC1 (BAC) | CT1812 (amyloid beta oligomer receptor antagonist) | E2027 (PDE9 inhibitor) |
| E2609 (BACE1 protein inhibitor) | EVT302 (MAO-B inhibitor) | gantenerumab (amyloid beta-protein inhibitor) | GC021109 (purinoceptor P2Y6 agonist) |
| HSRx-888 (donepezil/food-based compound) | immune globulin/albumin | LNP-102 intranasal | intepirdine (RVT-101) (serotonin 6 receptor antagonist) |
| IONIS-MAPTRx (tau-targeting protein) | JNJ-54861911 (BACE inhibitor) | JOT106 (oral capsule of trans-resveratrol) | KPAX002-2 (proprietary version of methylphenidate) |
| lanabecestat (BACE inhibitor) | LM11A-31 (p75 neutrophin receptor) | LMTX (tau protein aggregation inhibitor/TDP-43 aggregation inhibitor) | LY3002813 (N3pG-amyloid beta antibody) |
| LY3202626 (BACE inhibitor) | LY3303560 (tau antibody) | M1 agonist (selective M1 receptor agonist) | MEDI1814 (anti-amyloid beta 42 mAb) |
| mesenchymal stem cell therapy | MP-101 (mGluR2/mGluR3 agonist) | MSDC-0160 (mTOT modulator) | NBXT-001 + Nobilis ™ inhalation device (NMDA receptor antagonist) |
| neflamapimod (VX-745) (p38 mitogen-activated protein kinase inhibitor) | NGP 555 (gamma secretase complex modulator) | nilvadipine soluble amyloid reducing/clearing agent) | NPT088 (GAIM Ig fusion targeting amyloid-β, tau, a-synuclein) |
| Nuplazid ® pimavanserin | PF-05251749 (casein kinase 1 delta/epsilon) | PF-06648671 (gamma secretase complex modulator) | PF-06751979 (enzyme inhibitor) |
| pioglitazone (low-dose) (PPARγ agonist) | piromelatine (melatonin agonist) | Posiphen ® R-phenserine | Rexulti ® brexpiprazole |
| RG6100 (tau protein inhibitor) | RVT-103 + RVT-104 (QAAM + cholinesterase inhibitor) | SAR228810 (anti-protofibrillar AB mAb) | selective BACE 1 inhibitor |
| solanezumab (amyloid beta protein inhibitor) | SUVN-502 (serotonin 6 receptor antagonist) | SUVN-D4010 (serotonin 4 receptor agonist) | SUVN-G3031 (histamine H3 receptor antagonist) |
| T-817MA (amyloid beta-protein inhibitor) | T3D-959 (PPAR-delta/gamma agonist) | TAK-071 (muscarinic M1 receptor modulator) | TPI 287 (next-generation taxane) |
| UB-311 (anti-amyloid endobody vaccine) | UE-2343 (11β-HSD1 inhibitor) | verubecestat (MK-8931) (BACE1 protein inhibitor) | |

In another aspect, provided herein is a method of treating Alzheimer's disease in a human patient suffering from Alzheimer's disease, the method comprising administering to the human patient an effective amount of a hydroxypropyl-beta-cyclodextrin composition, wherein the hydroxypropyl-beta-cyclodextrin composition comprises a mixture of two or more hydroxypropyl-beta-cyclodextrin species, and wherein the mixture of two or more hydroxypropyl-beta-cyclodextrin species has a molar substitution value from about 0.59 to about 0.73.

In certain embodiments, the hydroxypropyl-beta-cyclodextrin composition further comprises 2.5% w/w or less of propylene glycol. In certain embodiments, the hydroxypropyl beta-cyclodextrin composition comprises a mixture of two or more hydroxypropyl beta-cyclodextrin species, wherein each of the two or more hydroxypropyl beta-cyclodextrin species has a different degree of hydroxypropylation of the beta-cyclodextrin ring, and wherein the hydroxypropyl-beta-cyclodextrin composition comprises 0.15% w/w or less of unsubstituted beta-cyclodextrin.

In another aspect, the hydroxypropyl beta-cyclodextrin composition comprises a mixture of two or more hydroxypropyl beta-cyclodextrin species, wherein each of the two or more hydroxypropyl beta-cyclodextrin species has a different degree of hydroxypropylation of the beta-cyclodextrin ring, wherein the mixture of two or more hydroxypropyl beta-cyclodextrin species has a molar substitution value from about 0.59 to about 0.73, and wherein the hydroxypropyl beta-cyclodextrin composition comprises 2.5% w/w or less of propylene glycol and 0.15% w/w or less of unsubstituted beta-cyclodextrin.

In a further aspect, provided herein is a method of treating Alzheimer's disease in a human patient suffering from Alzheimer's disease, the method comprising:

(a) administering to the human patient an initial dose of a hydroxypropyl-beta-cyclodextrin composition; and
(b) administering to the human patient the hydroxypropyl-beta-cyclodextrin composition in a monthly escalating dose regimen until a maximum tolerated dose is determined.

In certain embodiments, the method further comprises subsequently administering the maximum tolerated dose to the human patient.

In another aspect, provided herein is a method of treating Alzheimer's disease in a human patient suffering from Alzheimer's disease, the method comprising:

(a) administering to the human patient an initial 500 mg/kg dose by parenteral administration or an initial dose of 100 mg by CNS administration, of a hydroxypropyl-beta-cyclodextrin composition; and
(b) administering to the human patient the hydroxypropyl-beta-cyclodextrin composition in a monthly escalating dose regimen until a maximum tolerated dose is determined.

In a further aspect, provided herein is a method of treating Alzheimer's disease in a human patient suffering from Alzheimer's disease, the method comprising:

(a) administering to the human patient an initial 500 mg/kg dose of a hydroxypropyl-beta-cyclodextrin composition; and
(b) administering to the human patient the hydroxypropyl-beta-cyclodextrin composition in a monthly escalating dose regimen until a maximum tolerated dose is determined, wherein the monthly escalating dose regimen comprises administering to the human patient a 500 mg/kg dose one month after the initial dose, 1,000 mg/kg doses two and three months after the initial dose, 1,500 mg/kg doses four and five months after the initial dose, 2,000 mg/kg doses six and seven months after the initial dose and 2,500 mg/kg doses eight and nine months after the initial dose.

In certain embodiments, the method further comprises administering the maximum tolerated dose of the hydroxypropyl-beta-cyclodextrin composition once a month for 3 months, 4 months, 5 months, 6 months, 7 months, 8 months, 9 months, 10 months, 11 months, or 12 months. In some embodiments, the method further comprises administering the maximum tolerated dose of the hydroxypropyl-beta-cyclodextrin composition once a month for up to the duration of the life span of the human patient.

In a further aspect, provided herein is method of treating Alzheimer's disease in a subject suffering from Alzheimer's disease comprising
(a) administering an effective amount of a hydroxypropyl-beta-cyclodextrin composition; and
(b) administering an effective amount of a second therapeutic agent.

In certain embodiments, the second therapeutic agent is selected from the group consisting of donepezil, rivastigmine, galantamine, memantine, verubecestat, solanezumab, bapineuzumab, aducanumab, tideglusib, epothilone D and ABBV-8E12. In some embodiments, the second therapeutic agent is selected from the group consisting of a cholinesterase inhibitor, an NMDA receptor antagonist, a humanized antibody which targets tau protein, a humanized antibody which targets amyloid beta protein, and a BACE inhibitor. In some embodiments, the second therapeutic agent is selected from the group consisting of Aricept®, Namenda®, donepezil, memantine, Excelon®, Namenda® XR, galantamine, Aricept® ODT, rivastigmine, vitamin e, Razadyne® ER, donepezil/memantine, Razadyne®, Namzaric®, Alpha E®, Hydergine®, ergoloid mesylates, Aqua®-E, Aqua Gem-E®, etanercept, Reminyl®, Vita-Plus E natural, Aquasol E®, Aquavite-E® and E-400 clear.

In certain embodiments, the disclosure provides features a method of reducing Aβ production in a subject, the method comprising administering to the subject an effective amount of a hydroxypropyl-beta-cyclodextrin composition.

In certain embodiments, the method comprises administering to a subject in need thereof an effective amount of a hydroxypropyl-beta-cyclodextrin composition decreases Aβ production by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%.

In certain embodiments, the method comprises administering to the patient in need thereof an effective amount of a hydroxypropyl beta-cyclodextrin composition decreases Aβ plaque deposition by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%.

In certain embodiments, the method comprises administering to a subject in need thereof an effective amount of a hydroxypropyl beta-cyclodextrin composition reduces Tau accumulation by 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100%.

In certain embodiments, the method comprises administering to a subject in need thereof an effective amount of a hydroxypropyl beta-cyclodextrin composition stabilizes the progression of Alzheimer's disease in the subject in need thereof.

In some embodiments, the method comprises administering to a subject in need thereof an effective amount of a hydroxypropyl beta-cyclodextrin composition increases cognitive function in the subject in need thereof by about 1%, about 2%, about 3%, about 4%, about 5%, about 6%, about 7%, about 8%, about 9%, about 10%, about 15%, about 20%, about 25%, about 30%, about 40%, about 45%, about 50%, about 60%, about 65%, about 70%, about 75%, about 80%, about 85%, about 90%, about 95%, or about 100% when compared to the cognitive function of the subject prior to administration of the hydroxypropyl beta-cyclodextrin composition.

In some embodiments, administering to a subject in need thereof an effective amount of a hydroxypropyl beta-cyclodextrin composition increases cognitive function in the subject in need thereof by about 1-fold, about 2-fold, about 3-fold, about 4-fold, about 5-fold, about 6-fold, about 7-fold, about 8-fold, about 9-fold, about 10-fold, about 20-fold, about 30-fold, about 40-fold, about 50-fold, about 60-fold, about 70-fold, about 80-fold, about 90-fold, about 100-fold, about 200-fold, about 300-fold, about 400-fold, about 500-fold, about 600-fold about 700-fold, about 800-fold, about 900-fold, about 1000-fold, about 10000-fold, about 100000-fold, or about 1000000-fold, when compared to the cognitive function of the subject prior to administration of the hydroxypropyl beta-cyclodextrin composition.

Pharmaceutical Compositions

In one aspect, the disclosure provides pharmaceutical compositions for the treatment of Alzheimer's disease in a subject suffering from Alzheimer's disease, comprising an effective amount of a hydroxypropyl beta-cyclodextrin composition disclosed herein. In some embodiments, the subject is a human patient.

In some embodiments, the pharmaceutical composition comprises about 25 mg, about 50 mg, about 75 mg, about 100 mg, about 150 mg, about 200 mg, about 250 mg, about 300 mg, about 350 mg, about 400 mg, about 450 mg, about 500 mg, about 600 mg, about 700 mg, about 800 mg, about 900 mg, about 1000 mg, about 1250 mg, about 1500 mg, about 1750 mg, about 2000 mg, about 2250 mg, about 2500 mg, about 2750 mg, or about 3000 mg of the hydroxypropyl-beta-cyclodextrin composition.

In some embodiments, the pharmaceutical composition comprises from about 25 mg to about 2500 mg, about 250 mg to about 2500 mg, about 500 mg to about 2500 mg, about 750 mg to about 2500 mg, about 1000 mg to about 2500 mg, about 1250 mg to about 2500 mg, about 1500 mg to about 2500 mg, about 1750 mg to about 2500 mg, about 2000 mg to about 2500 mg, about 2250 mg to about 2500 mg, about 25 mg to about 2250 mg, about 25 mg to about 2000 mg, about 25 mg to about 1750 mg, about 25 mg to about 1500 mg, about 25 mg to about 1250 mg, about 25 mg to about 1000 mg, about 25 mg to about 750 mg, about 25 mg to about 500 mg, about 500 mg to about 2250 mg, about 500 mg to about 2000 mg, about 500 mg to about 1750 mg, about 500 mg to about 1500 mg, about 500 mg to about 1250 mg, about 500 mg to about 1000 mg, about 500 mg to about 750 mg, about 750 mg to about 2250 mg, about 750 mg to about 2000 mg, about 750 mg to about 1750 mg, about 750 mg to about 1500 mg, about 750 mg to about 1250 mg, about 750 mg to about 1000 mg, about 1000 mg to about 2250 mg, about 1000 mg to about 2000 mg, about 1000 mg to about 1750 mg, about 1000 mg to about 1500 mg, about 1000 mg to about 1250 mg, about 1250 mg to about 2250 mg, about 1250 mg to about 2000 mg, about 1250 mg to about 1750 mg, about 1250 mg to about 1500 mg, 1500 mg to about 2250 mg, 1500 mg to about 2000 mg, 1500 mg to about 1750 mg, about 1750 mg to about 2250 mg, about 1750 mg to about 2000 mg, or about 2000 mg to about 2250 mg of the hydroxypropyl beta-cyclodextrin composition.

In certain embodiments, the hydroxypropyl beta-cyclodextrin composition comprises a 5% (w/v), 10% (w/v), 15% (w/v), 20% (w/v), 25% (w/v), 30% (w/v), 35% (w/v) or 40% (w/v) aqueous solution of one or more hydroxypropyl beta-cyclodextrin species. In some embodiments, the effective amount of the hydroxypropyl beta-cyclodextrin composition comprises a 25% (w/v) solution of one or more hydroxypropyl beta-cyclodextrin species. In some embodiments, the 25% (w/v) solution of one or more hydroxypropyl beta-cyclodextrin species is a 25% (w/v) aqueous solution of one or more hydroxypropyl beta-cyclodextrin species.

In certain embodiments, the pharmaceutical compositions of the present invention further comprise one or more pharmaceutically acceptable excipients. In some embodiments, the one or more pharmaceutically acceptable excipients is selected from the group comprising a diluent, a buffering agent, a preservative, a stabilizer, a solubilizing agent or any combination thereof.

In certain embodiments, the pharmaceutical composition may be formulated for administration as a liquid dosage form suitable for intracavitary, intradermal, intramuscular, intrathecal, intravenous, subcutaneous, or intracerebroventricular administration.

In certain embodiments, a liquid dosage form of a pharmaceutical composition as described herein further comprises a diluent. In some embodiments, the insert diluent is a saline solution.

In certain embodiments, a liquid dosage form of a pharmaceutical composition as described herein further comprises a buffering agent. For example, suitable buffering agents for use with the present disclosure include, but are not limited to, both organic and inorganic acids and salts thereof, such as citrate buffers (e.g., monosodium citrate-disodium citrate mixture, citric acid-trisodium citrate mixture, citric acid-monosodium citrate mixture), succinate buffers (e.g., succinic acid-monosodium succinate mixture, succinic acid-sodium hydroxide mixture, succinic acid-disodium succinate mixture), tartrate buffers (e.g., tartaric acid-sodium tartrate mixture, tartaric acid-potassium tartrate mixture, tartaric acid-sodium hydroxide mixture), fumarate buffers (e.g., fumaric acid-monosodium fumarate mixture, fumaric acid-disodium fumarate mixture, monosodium fumarate-disodium fumarate mixture), gluconate buffers (e.g., gluconic acid-sodium gluconate mixture, gluconic acid-sodium hydroxide mixture, gluconic acid-potassium gluconate mixture), oxalate buffer (e.g., oxalic acid-sodium oxalate mixture, oxalic acid-sodium hydroxide mixture, oxalic acid-potassium oxalate mixture, etc.), lactate buffers (e.g., lactic acid-sodium lactate mixture, lactic acid-sodium hydroxide mixture, lactic acid-potassium lactate mixture, etc.) and acetate buffers (e.g., acetic acid-sodium acetate mixture, acetic acid-sodium hydroxide mixture, etc.). Additionally, phosphate buffers, histidine buffers and trimethylamine salts such as Tris may be used.

In certain embodiments, a liquid dosage form of a pharmaceutical composition as described herein further comprises a preservative. For example, suitable preservatives for use with the present disclosure include, but are not limited to phenol, benzyl alcohol, meta-cresol, methyl paraben, propyl paraben, octadecyldimethylbenzyl ammonium chloride, benzalkonium halides (e.g., chloride, bromide, and iodide), hexamethonium chloride, and alkyl parabens (e.g., methyl or propyl paraben, catechol, resorcinol, cyclohexanol, and 3-pentanol).

In certain embodiments, a liquid dosage form of a pharmaceutical composition as described herein further comprises a stabilizer. For example, suitable stabilizers include, but are not limited to polyhydric sugar alcohols, trihydric or higher sugar alcohols, amino acids, organic sugars or sugar alcohols, polyvinylpyrrolidone monosaccharides, trisaccharides, polysaccharides, proteins, sulfur containing reducing agents, amino acid polymers and polyethylene glycol.

In certain embodiments, a liquid dosage form of a pharmaceutical composition as described herein further comprises a solubilizing agent. In some embodiments, the solubilizing agent is an ionic surfactant. Examples of non-ionic surfactants include, but are not limited to, polysorbates, poloxamers, pluronic polyols, and polyoxyethylene sorbitan monoethers.

In certain embodiments, pharmaceutical compositions of the hydroxypropyl beta-cyclodextrin compositions disclosed herein can be prepared for storage as lyophilized formulations or aqueous solutions by mixing the hydroxypropyl beta-cyclodextrin composition with optional pharmaceutically-acceptable carriers, excipients or stabilizers typically employed in the art (e.g., buffering agents, stabilizing agents, preservatives, isotonifiers, non-ionic detergents, antioxidants, and other miscellaneous additives).

In certain embodiments, the pharmaceutical compositions described herein further comprise a second therapeutic agent. In some embodiments, the second therapeutic agent is indicated to treat Alzheimer's disease. In some embodiments, the second therapeutic agent is selected from the group consisting of donepezil, rivastigmine, galantamine, memantine, verubecestat, solanezumab, bapineuzumab, aducanumab, tideglusib, epothilone D and ABBV-8E12. In some embodiments, the second therapeutic agent is selected from the group consisting of a cholinesterase inhibitor, an NMDA receptor antagonist, a humanized antibody which targets tau protein, a humanized antibody which targets amyloid beta protein, and a BACE inhibitor. In some embodiments, the second therapeutic agent is selected from the group consisting of Aricept®, Namenda®, donepezil, memantine, Excelon®, Namenda XR®, galantamine, Aricept® ODT, rivastigmine, vitamin e, Razadyne® ER, donepezil/memantine, Razadyne®, Namzaric®, Alpha E®, Hydergine®, ergoloid mesylates, Aqua-E®, Aqua Gem-E®, etanercept, Reminyl®, Vita-Plus E natural, Aquasol E®, Aquavite-E® and E-400 clear.

In some embodiments, the second therapeutic agent is selected from any therapeutic agent set forth in Table 1.

In certain embodiments, the second therapeutic agent is selected from the group consisting of ABBV-8E12 (anti-tau antibody), AC-1204 (glucose stimulant), ACI-24 (anti-Abeta vaccine), ACI-35 (anti-pTau vaccine), aducanumab (BIIB037) (amyloid beta mAb), AGB101 (levetiracetam low-dose), ALZ-801 (amyloid beta-protein inhibitor), ALZT-OP1 (amyloid beta-protein inhibitor/inflammation mediator inhibitor), AMG520/CNP520 (BACE1 protein inhibitor), ANAVEX™ 2-73 (M1 muscarinic receptor agonist/intracellular sigma 1 receptor agonist), AstroStem (mesenchymal stem cell therapy, AUS-131 (nonhormonal estrogen receptor agonist), AVN-101 (serotonin 6 receptor antagonist), AVN-322 (serotonin 6 receptor antagonist), AVP-786 (dextromethorphan analogue/ultra-low dose quinidine), AXS-05 (bupropion/dextromethorphan), azeliragon (TTP488) (RAGE antagonist), BAN2401 (anti-amyloid beta mAb), Bexarotene (RXR-selective retinoid analogue), BI 409306 (PDE9A inhibitor), BIIB076 (anti-tau antibody), BIIB092 (anti-extracellular tau antibody), BNC375 (positive allosteric modulator), BPN14770 (type 4 cyclic nucleotide phosphodiesterase inhibitor), bryostatin 1 (protein kinase C stimulant), CAD106 (amilomotide) (VLP immunotherapy vaccine), Corplex Donepezil (donepezil transdermal patch, Corplex Memantine (memantine transdermal patch, CPC-201 (donepezil/solifenacin combination), CPC-212 (next-generation acetylcholinesterase inhibitor), CPC-250 (next-generation acetylcholine-sterase inhibitor), Crenezumab (anti-amyloid beta antibody), CSP-1103 (amyloid beta-protein inhibitor), CSTC1 (BAC), CT1812 (amyloid beta oligomer receptor antagonist), E2027 (PDE9 inhibitor), E2609 (BACE1 protein inhibitor), EVT302 (MAO-B inhibitor), gantenerumab (amyloid beta-protein inhibitor), GC021109 (purinoceptor P2Y6 agonist), HSRx-888 (donepezil/food-based compound), immune globulin/albumin, INP-102 intranasal, intepirdine (RVT-101) (serotonin 6 receptor antagonist), IONIS-MAPTRx (tau-targeting protein), JNJ-54861911 (BACE inhibitor), JOT106 (oral capsule of trans-resveratrol), KPAX002-2 (proprietary version of methylphenidate), lanabecestat (BACE inhibitor), LM11A-31 (p75 neutrophin receptor), LMTX (tau protein aggregation inhibitor/TDP-43 aggregation inhibitor), LY3002813 (N3pG-amyloid beta antibody), LY3202626 (BACE inhibitor), LY3303560 (tau antibody), M1 agonist (selective M1 receptor agonist), MEDI1814 (anti-amyloid beta 42 mAb), mesenchymal stem cell therapy, MP-101 (mGluR2/mGluR3 agonist), MSDC-0160 (mTOT modulator), NBXT-001+Nobilis™ inhalation device (NMDA receptor antagonist), neflamapimod (VX-745) (p38 mitogen-activated protein kinase inhibitor), NGP 555 (gamma secretase complex modulator), nilvadipine soluble amyloid reducing/clearing agent), NPT088 (GAIM Ig fusion targeting amyloid-ß, tau, a-synuclein), Nuplazid® pimavanserin, PF-05251749 (casein kinase 1 delta/epsilon), PF-06648671 (gamma secretase complex modulator), PF-06751979 (enzyme inhibitor), pioglitazone (low-dose) (PPARγ agonist), piromelatine (melatonin agonist), Posiphen® R-phenserine, Rexulti® brexpiprazole, RG6100 (tau protein inhibitor), RVT-103+RVT-104 (QAAM+cholinesterase inhibitor), SAR228810 (anti-protofibrillar Aβ mAb), selective BACE 1 inhibitor, solanezumab (amyloid beta protein inhibitor), SUVN-502 (serotonin 6 receptor antagonist), SUVN-D4010 (serotonin 4 receptor agonist), SUVN-G3031 (histamine H3 receptor antagonist), T-817MA (amyloid beta-protein inhibitor), T3D-959 (PPAR-delta/gamma agonist), TAK-071 (muscarinic M1 receptor modulator), TPI 287 (next-generation taxane), UB-311 (anti-amyloid endobody vaccine), UE-2343 (11ß-HSD1 inhibitor), verubecestat (MK-8931) (BACE1 protein inhibitor), or combinations thereof.

In certain embodiments, the pharmaceutical compositions of the present disclosure are administered to the subject by intracavitary, intradermal, intramuscular, intrathecal, intravenous, subcutaneous, or intracerebroventricular administration.

Kits

In various embodiments, the invention provides kits for treating Alzheimer's disease in a subject suffering from Alzheimer's disease. In some embodiments, the kit comprises: i) instructions for administering the hydroxypropyl beta-cyclodextrin compositions or pharmaceutical compositions as described herein to a subject suffering from Alzheimer's disease, and ii) a hydroxypropyl beta-cyclodextrin composition or a pharmaceutical composition as described herein. In some embodiments, the kit may comprise one or more unit dosage forms containing an amount of a hydroxypropyl beta-cyclodextrin composition or a pharmaceutical composition as described herein that is effective for treating Alzheimer's disease in a subject. In some embodiments, the subject is a human patient.

In some embodiments, the kit comprises: i) instructions for administering the hydroxypropyl beta-cyclodextrin compositions or pharmaceutical compositions as described herein to subject suffering from Alzheimer's disease, and (ii) one or more 100 mL vials comprising 25% (w/v) of a hydroxypropyl beta-cyclodextrin composition or a pharmaceutical composition as described herein. In some embodiments, the hydroxypropyl beta-cyclodextrin composition or the pharmaceutical composition comprises the Trappsol® Cyclo™ hydroxypropyl beta-cyclodextrin composition.

In some embodiments, the kit further comprises one or more selected from the group comprising a sterile syringe, a sterile needle, a sterile IV bag, an infusion pump or any combination thereof.

The description above describes multiple aspects and embodiments of the present invention, including hydroxypropyl beta-cyclodextrin compositions, methods of using a hydroxypropyl beta-cyclodextrin compositions to treat a subject with Alzheimer's disease, pharmaceutical compositions comprising a hydroxypropyl beta-cyclodextrin compositions, and kits. The patent application specifically contemplates all combinations and permutations of the aspects and embodiments.

EXAMPLES

In order that the disclosure described herein may be more fully understood, the following examples are set forth. The synthetic and biological examples described in this application are offered to illustrate the compounds, pharmaceutical compositions, and methods provided herein and are not to be construed in any way as limiting their scope.

Example 1. Treating Alzheimer's Disease in a Geriatric Patient with a Hydroxypropyl-Beta-Cyclodextrin Composition 1. Informed Consent and Baseline Assessments The patient provides informed consent and then undergoes baseline assessments to reconfirm the lack of any contraindications to receiving treatment under this protocol. Specifically, the patient is assessed at baseline with a clinical and neurological examination as well as routine clinical laboratory studies (e.g., CBC, complete metabolic panel, PT/INR, lipids, urinalysis) and an electrocardiogram (ECG). MRI data collected in the previous 3 months is reviewed and audiology baseline on file. The status of the Alzheimer's disease is assessed using the mini-mental state examination (MMSE).

2. Product Preparation and Use Procedures

The patient is administered Trappsol® Cyclo™ 2-hydroxypropyl-β-cyclodextrin.

Trappsol® Cyclo™ is prepared aseptically according to the pharmacy manual. In brief, 100 ml vials of 25% (w/v) Trappsol® Cyclo™ are combined with saline to reach the desired volume (Pharmacy Manual).

Using a sterile technique, an ordered dose of Trappsol® Cyclo™ HPβCD is drawn up using 60 cc Luer-lock syringes and a 16 G needle.

The total ordered dose is then added to a 500 mL (doses <100 mg/kg) or a 1000 mL (such as Baxter or Intravia) IV bag using 18 G needles.

After the total ordered dose has been added to the IV bag, all the air is removed from the IV bag.

The IV bag is then be labeled and a pharmacist performs a final check.

3. Treatment Plan

Trappsol® Cyclo™ is administered to the patient via IV infusion. The initial dose is 500 mg/kg (T=Day 0).

Thereafter, the Trappsol® Cyclo™ is administered to the patient using a dose escalation protocol to determine the maximum dose level. Each escalation of dose is based on clinical and laboratory assessments, monitoring of toxicity and following review of benefit/risk ratio after the initial increase in dose and prior to each subsequent dose level. This new elevated dose level is either held at this level or continued to the next assigned level. Only after two (2) same dose levels are given, is the next following dose increased to the next dose escalation level. This may continue until the maximum of 2500 mg/kg of IV HPβCD is reached. The dose escalation protocol is shown in Table 2.

TABLE 2

Dosing schedule.

| Dose Number | Month | Dose Amount (mg/kg) |
| --- | --- | --- |
| 1 | 0 | 500 |
| 2 | 1 | 500 |
| 3 | 2 | 1000 |
| 4 | 3 | 1000 |
| 5 | 4 | 1500 |
| 6 | 5 | 1500 |
| 7 | 6 | 2000 |
| 8 | 7 | 2000 |
| 9 | 8 | 2500 (target dose level) |
| 10 | 9 | 2500 |

4. Post-Infusion Monitoring

At least one physician and another qualified personnel are present during each of the infusions to monitor, assess and respond to any adverse events. The patient receives vital signs monitoring and pulse oximetry during each infusion. A crash cart for cardiopulmonary resuscitation is available, and the physician is trained in advanced life support.

The patient receives a physical exam at 24 and 72 hours post each infusion. During the dose escalation phase of the study, blood is drawn for pharmacokinetic and pharmacodynamic markers pre-dose, at 4 hours and 8 hours after the start of infusion, and at 1 hour and 24 hours following infusion.

5. Safety Assessments

The patient is monitored periodically throughout the course of treatment. The following safety assessments are performed:

adverse events weight and height: obtained at baseline, month 6 and month 12 vital signs: (e.g., blood pressure, pulse, temperature, heart rate, respiratory rate) vital signs are taken with the subject in the sitting position after 5 minutes of rest. Vitals are measured every 15 minutes for the first 2 hours of infusion then every 2 hours thereafter until completion of post-infusion observation period.

neurologic exam including a cognitive assessment: mental status tests laboratory tests: CBC, serum chemistry panel including LFTS, coagulation panel, urinalysis, lipid.

ECG: single lead during dosing. ECG is performed at baseline and prior to each monthly infusion during the dose escalation period and once reaching maximum dose, and month 12.

MRI: without gadolinium for safety monitoring. A clinical MRI, for the purpose of safety assessments, is performed at month 3, 6 and 12 months.

audiology: at 3 months and as clinically indicated to monitor for hearing loss.

6. Disease Activity Monitoring

In order to assess risk/benefit of this treatment plan, the patient is monitored on a regular basis for any changes in the underlying disease process. The following parameters are assessed:

mini mental state examination: The MMSE is used to evaluate the cognitive function. Assessments are scheduled at baseline, and months 3, 6, 9, 12 and every 6 months thereafter.

amyloid/Tau PET scanning: the patient has baseline Tau and amyloid PET imaging completed. Repeat amyloid PET imaging (florbetapir) and AV-1451 are completed at month (twelve) 12 and compared to pre-treatment amyloid and tau PET imaging to measure change in amyloid and tau deposition.

Precursors of cholesterol metabolism are measured in serum at pre-dose, 24, 48, 72 hours post-dose: desmosterol, lanosterol, lathosterol at the central lab and through validated measures.

24-(S) Hydroxycholesterol (24(S)—HC) is measured in plasma using a liquid chromatography-tandem mass spectrometry (LC-MS/MS) assay. Blood is collected for 24(S)—HC analysis at the following time points: pre-dose, 24, 48, and 72 hours post. 24(S)—HC may also be measured on the samples collected for PK analysis.

Serum levels of non-enzymatically formed cholesterol oxidation products, specifically 7-ketocholesterol and cholestane-3β,5α,6β-triol are measured by LC-MS/MS. Blood is collected for oxysterol analysis at the following time points: pre-dose, 24, 48, and 72 hours post-dose. For oxysterol sampling, 3 mL of blood is obtained for each time point. Thus a total volume per initial infusion is ≤21 mL on Day 0 and ≤9 mL over the next 3 days. Oxysterols may also be measured on the samples collected for PK analysis.

7. Therapeutic End Point

The primary endpoint of this treatment plan is 1) safety and 2) tolerability in general physical, neurological and cognitive functioning. Arrest of disease progression is assessed based upon comparison of pre- and post-treatment examinations including physical exam, memory testing (MMSE) and laboratory assessments. Amyloid and Tau PET CT scans are obtained at month 12 for comparison to baseline amyloid and Tau PET CT imaging for measurement of change in SUVR.

Example 2. Treating Alzheimer's Disease in a Geriatric Patient with Intravenous (IV) Trappsol® Cyclo™ 2-Hydroxypropylβ-Cyclodextrin (HPβCD)

1. Patient Summary Information

The patient is an 82 year-old man with dementia due to Alzheimer's disease who has continued to decline while being treated with standard therapies for the treatment of Alzheimer's disease.

2. Baseline Assessments

The patient underwent baseline assessments to reconfirm the lack of any contraindications to receiving treatment under this protocol. Specifically, the patient was assessed at baseline with a clinical and neurological examination as well as routine clinical laboratory studies (e.g., complete blood count ("CBC"), complete metabolic panel, prothrombin time/international normalized ratio ("PT/INR"), lipids, urinalysis) and an electrocardiogram (ECG). MRI data collected in the previous 3 months was reviewed and audiology baseline on file. The status of the Alzheimer's disease was assessed using the mini-mental state examination (MMSE).

3. Product Preparation and Use Procedures

The patient was administered Trappsol® Cyclo™ 2-hydroxypropyl-β-cyclodextrin.

Trappsol® Cyclo™ was prepared aseptically: 100 ml vials of 25% (w/v) Trappsol® Cyclo™ were combined with saline to reach the desired volume.

Using a sterile technique, an ordered dose of Trappsol® Cyclo™ HPβCD was drawn up using 60 cc Luer-lock syringes and a 16 G needle.

The total ordered dose was then added to a 500 mL (doses <100 mg/kg) or a 1000 mL (such as Baxter or Intravia) IV bag using 18 G needles, and all air was removed from the IV bag 4. Treatment Plan The patient was dosed initially with 500 mg/kg of Trappsol® Cyclo™ by intravenous administration over an 8 hour infusion period.

Thereafter, the Trappsol® Cyclo™ was administered to the patient using a dose escalation protocol to determine the maximum dose level. Each escalation of dose was based on clinical and laboratory assessments, monitoring of toxicity and following review of benefit/risk ratio after the initial increase in dose and prior to each subsequent dose level. This new elevated dose level was either held at this level or continued to the next assigned level. Only after two (2) doses at the same level was given, was the next following dose increased to the next dose escalation level. The patient's dosing schedule is shown in Table 3.

The patient tolerated the dose escalation to a dose of 1500 mg/kg IV Trappsol® Cyclo™ at month 5 at which time there were possible tolerability issues. The dose was decreased to 500 mg/kg for months 6 and 7, increased to 1000 mg/kg for month 8, then reduced to 750 mg/kg which was further reduced to 500 mg/kg for month 9 and then increased to 750 mg/kg which was well tolerated for months 10 and 11.

5. Post-Infusion Monitoring

At least one physician and another qualified personnel were present during each of the infusions to monitor, assess and respond to any adverse events. The patient received vital signs monitoring and pulse oximetry during each infusion.

The patient received a physical exam at 24 and 72 hours post each infusion. During the dose escalation phase of the study, blood was drawn for pharmacokinetic and pharmacodynamic markers pre-dose, at 4 hours and 8 hours after the start of infusion, and at 1 hour and 24 hours following infusion.

6. Safety Assessments

The patient was monitored periodically throughout the course of treatment. The following safety assessments were performed:

adverse events weight and height: obtained at baseline, month 6 and month 12 vital signs (e.g., blood pressure, pulse, temperature, heart rate, respiratory rate: vital signs were taken with the subject in the sitting position after 5 minutes of rest. Vital signs were measured every 15 minutes for the first 2 hours of infusion then every 2 hours thereafter until completion of post-infusion observation period.

neurologic exam including a cognitive assessment: mental status tests laboratory tests: CBC, serum chemistry panel including, liver function tests ("LFTs"), coagulation panel, urinalysis, lipid.

ECG: single lead during dosing. ECG was performed at baseline and prior to each monthly infusion during the dose escalation period and once reaching maximum dose, and month 12.

MRI: without gadolinium for safety monitoring. A clinical MRI, for the purpose of safety assessments, was performed at baseline, 3 months, and 12 months.

audiology: at 3 months and as clinically indicated to monitor for hearing loss.

assessments of suicidal ideation and behavior: monthly

Changes in blood biomarkers.

pharmacokinetic data: The peak pK value occurred at the end of the 8-hour infusion.

TABLE 3

Dosing Schedule

| Dose Number | Month | Dose Amount (mg/kg) |
|---|---|---|
| 1 | 0 | 500 |
| 2 | 1 | 500 |
| 3 | 2 | 1000 |
| 4 | 3 | 1000 |
| 5 | 4 | 1500 |
| 6 | 5 | 1500 |
| 7 | 6 | 500 |
| 8 | 7 | 500 |
| 9 | 8 | 1000 |
| 10 | 9 | 750 then reduced to 500 |
| 11 | 10 | 750 |
| 12 | 11 | 750 |

TABLE 4

Pharmacokinetic Data

| Visit | Day Nominal | Hour Nominal | Analyte | Concentration (µg/mL) |
|---|---|---|---|---|
| Day 0 | 0 | 0 | HPBCD | BLQ |
| Day 0 | 0 | 4 | HPBCD | 684 |
| Day 0 | 0 | 8 | HPBCD | 911 |
| Day 0 | 0 | 24 | HPBCD | 32.0 |
| Month 1 | 0 | 0 | HPBCD | BLQ |
| Month 1 | 0 | 1 | HPBCD | 728 |
| Month 1 | 0 | 4 | HPBCD | 697 |
| Month 1 | 0 | 8 | HPBCD | 976 |
| Month 1 | 0 | 24 | HPBCD | 39.9 |
| Month 2 | 0 | 0 | HPBCD | BLQ |
| Month 2 | 0 | 1 | HPBCD | 1560 |
| Month 2 | 0 | 4 | HPBCD | 1310 |

TABLE 4-continued

Pharmacokinetic Data

| Visit | Day Nominal | Hour Nominal | Analyte | Concentration (µg/mL) |
|---|---|---|---|---|
| Month 2 | 0 | 8 | HPBCD | 2130 |
| Month 2 | 0 | 24 | HPBCD | 91.3 |
| Month 3 | 0 | 0 | HPBCD | 0.0986 |
| Month 3 | 0 | 1 | HPBCD | 1990 |
| Month 3 | 0 | 4 | HPBCD | 683 |
| Month 3 | 0 | 8 | HPBCD | 2550 |
| Month 3 | 0 | 24 | HPBCD | 105 |
| Month 4 | 0 | 0 | HPBCD | 0.133 |
| Month 4 | 0 | 1 | HPBCD | 2570 |
| Month 4 | 0 | 4 | HPBCD | 2450 |
| Month 4 | 0 | 8 | HPBCD | 3520 |
| Month 4 | 0 | 24 | HPBCD | 121 |
| Month 5 | 0 | 0 | HPBCD | 0.211 |
| Month 5 | 0 | 1 | HPBCD | 2790 |
| Month 5 | 0 | 4 | HPBCD | 2410 |
| Month 5 | 0 | 8 | HPBCD | 3630 |
| Month 7 | 0 | 0 | HPBCD | 0.0804 |
| Month 7 | 0 | 1 | HPBCD | 708 |
| Month 7 | 0 | 4 | HPBCD | 687 |
| Month 7 | 0 | 8 | HPBCD | 992 |
| Month 7 | 0 | 24 | HPBCD | 37.6 |
| Month 8 | 0 | 0 | HPBCD | BLQ |
| Month 8 | 0 | 1 | HPBCD | 713 |
| Month 8 | 0 | 4 | HPBCD | 701 |
| Month 8 | 0 | 8 | HPBCD | 698 |
| Month 8 | 0 | 24 | HPBCD | 42.7 |
| Month 9 | 0 | 0 | HPBCD | 0.0872 |
| Month 9 | 0 | 1 | HPBCD | 1180 |
| Month 9 | 0 | 4 | HPBCD | 1200 |
| Month 9 | 0 | 8 | HPBCD | 1420 |
| Month 9 | 0 | 24 | HPBCD | 62.4 |
| Month 10 | 0 | 0 | HPBCD | BLQ |
| Month 10 | 0 | 1 | HPBCD | 825 |
| Month 10 | 0 | 4 | HPBCD | 849 |
| Month 10 | 0 | 8 | HPBCD | 1090 |
| Month 10 | 0 | 24 | HPBCD | 38.0 |
| Month 11 | 0 | 0 | HPBCD | 0.0787 |
| Month 11 | 0 | 1 | HPBCD | 1090 |
| Month 11 | 0 | 4 | HPBCD | 1100 |
| Month 11 | 0 | 8 | HPBCD | 1420 |
| Month 11 | 0 | 24 | HPBCD | 67.4 |
| Month 12 | 0 | 0 | HPBCD | 0.0896 |
| Month 12 | 0 | 4 | HPBCD | 772 |
| Month 12 | 0 | 8 | HPBCD | 1360 |
| Month 12 | 0 | 24 | HPBCD | 52.8 |

7. Disease Activity Monitoring

The patient was monitored on a regular basis for any changes in the underlying disease process. The following parameters were assessed:

Mini Mental State Examination: The MMSE was used to evaluate the patient's cognitive function. Assessments were scheduled at baseline, and months 3, 6, 9, 12 and every 6 months thereafter Precursors of cholesterol metabolism were measured in serum at pre-dose, 24, 48, 72 hours post-dose: desmosterol, lanosterol, lathosterol at the central lab and through validated measures.

24-(S) Hydroxycholesterol (24(S)—HC) was measured in plasma using a liquid chromatography-tandem mass spectrometry (LC-MS/MS) assay. Blood was collected for 24(S)—HC analysis at the following time points: pre-dose, 24, 48, and 72 hours post. 24(S)—HC was also measured on the samples collected for PK analysis.

Serum levels of non-enzymatically formed cholesterol oxidation products, specifically 7-ketocholesterol and cholestane-3β,5α,6β-triol were measured by LC-MS/MS. Blood was collected for oxysterol analysis at the following time points: pre-dose, 24, 48, and 72 hours post-dose. For oxysterol sampling, 3 mL of blood was obtained for each time point. Thus a total volume per initial infusion was ≤21 mL on Day 0 and ≤9 mL over the next 3 days. Oxysterols were also measured on the samples collected for PK analysis.

8. Therapeutic End Point

The primary endpoint of this treatment plan was 1) safety and 2) tolerability in general physical, neurological and cognitive functioning. Arrest of disease progression was assessed based upon comparison of pre- and post-treatment examinations including physical exam, memory testing (MMSE) and laboratory assessments.

9. Results (i) Dosing

Per the approved protocol, the patient was dosed initially with IV Trappsol® Cyclo™ HPβCD 500 mg/kg over an 8-hour infusion period for two monthly doses.

Pharmacokinetic data, safety data, biomarkers and adverse event data were reviewed by a Safety Review Committee prior to escalation of dose every 2 months during the initial 2-month study period. The patient tolerated the IV dosing regimen well. Safety labs, ECGs, and monthly clinical examinations showed no change from baseline and no evidence of toxicity. The patient tolerated the dose escalation to a dose of 1500 mg/kg IV Trappsol® Cyclo™ HPβCD at Month 5, at which time there was possible tolerability issues (see Adverse Events summary below). The dose was decreased to 500 mg/kg and titrated to 750 mg/kg and thereafter was well tolerated.

(ii) MRI Safety Assessments

Summary: The patient completed baseline and Month 3 brain MRI for safety assessments per the protocol. The baseline MRI showed moderate chronic small vessel ischemic disease with typical pattern of atrophy. The Month 3 follow-up safety MRI showed no change from baseline, with stable moderate chronic small vessel ischemic disease and two chronic infarcts that were stable and unchanged from baseline imaging. No evidence of amyloid related imaging abnormalities (ARIA E or H) were noted by the interpreting radiologist. The patient was clinically stable without sign of new neurologic deficits requiring repeat imaging.

Month 12 MRI:

Sagittal T1 images, axial FLAIR and T2-weighted images, axial diffusion-weighted images and coronal gradient-echo images of the brain were obtained without contrast administration. T1-weighted volumetric acquisition was performed and post processed using NeuroQuant software package. 3D sagittal images obtained under general physician supervision including monitoring and adjustment of the 3D structures and tissue types on an independent workstation.

The cerebral sulci and ventricles were mildly prominent. No midline shift, mass effect, extra-axial fluid collection, acute parenchymal bleeding or acute infarction or ischemia were present. Small focal regions of gliosis and encephalomalacia were observed in the right post central gyrus and the right paracentral lobule. There were T2/FLAIR hyperintensities within the periventricular and scattered subcortical white matter. Observation of foci of susceptibility within the body of the left lateral ventricle likely represented calcifications or old hemorrhage in the left choroid plexus.

There were postsurgical changes within both globes. Retention cysts were suspected within the right maxillary sinus and the bilateral ethmoid air cells. Mucosal thickening was present within the bilateral ethmoid air cells and the left maxillary sinus. The remaining paranasal sinuses and right mastoid air cells were clear. Trace fluid was present within the left mastoid air cells. No focal mass lesion was detected within the visualized nasopharynx. The major proximal intracranial vessels demonstrate flow voids indicating their patency.

There was hyperostosis frontalis interna.

The hippocampal volume normative percentile based on age-matched controls was 3.00%. The temporal horn volume normative percentile was 98.00%. These findings are suggestive of Alzheimer's disease.

The hippocampal volume nonnative percentile based on age-matched controls from the prior month 4 and month 10 examinations respectively where 4% and 20%. The temporal horn volume normative percentile on the prior 2 examinations respectively were 97% and 98%.

NeuroQuant substructure analysis:
Gray-white segmentation quality: Good
Whole brain structures (normative percentiles):
Whole brain: 68.00%
Gray matter: 87.00%
White matter: 30.00%
White matter hypointensities (black holes): (0.14% of intracranial volume)—60.00%
Cortical substructures below 2 standard deviations of normal (normative percentiles reported):
Left amygdala: 4%
Right hippocampus: 2%
0 of 24 noncortical brain subregions exhibit volumes below 2 standard deviations of normal.

Included in this analysis were 48 cortical and 24 noncortical brain substructures. Therefore, 3.5 substructures would be expected to be below 2 standard deviations from normal variation.

No acute intracranial abnormality was observed.

Mild cerebral volume loss and mild to moderate chronic microvascular ischemic change in the supratentorial white matter were similar to the prior examinations.

There were old small infarctions within the right parietal lobe that are similar to the prior examinations.

Quantitative analysis of brain substructure volumes revealed an increased number of substructures below 2 standard deviations of the mean: 2 cortical and 0 noncortical substructures, as reported above.

Quantitative automated analysis of hippocampal volume revealed findings suggestive of Alzheimer's disease. The patient's hippocampal volumes declined over the month 4 and month 10 examinations.

(iii) Audiology Safety Assessments

The patient completed baseline and Month 3 audiology testing for safety assessments per the protocol. The patient at baseline had age related hearing loss (presbycusis) that was stable at the Month 3 assessment and clinically stable during the 12-month study period. The patient was followed every 3 months by an ear, nose and throat (ENT) specialist for issues with wax build-up that was removed regularly to prevent hearing interference based upon an external factor. There was no evidence of hearing loss associated with the treatment dosing regimen.

(iv) Laboratory Safety Assessments

Monthly pre-infusion safety labs were collected and reviewed prior to dosing (CBC, chemistry panel, hematology, urinalysis, lipids, coagulation). There was lowering of the lipid panel as expected, with minimal change in the blood counts that were not a clinically significant change from baseline and no sign of systemic issues. No toxicity was noted to renal or hepatic organ systems and some mild fluctuation and improvement in baseline proteinuria present at baseline.

(v) ECG Safety Assessments

Monthly ECG monitoring showed no change from the baseline ECG of known atrial fibrillation, rate controlled. No QT prolongation, ischemic changes or evidence of cardiac system toxicity was observed during the 12-month study period.

(vi) Cognitive and Behavioral Assessments and Observations From Baseline Visit

Memory: memory assessments based upon mental status testing and clock draw (OCT) showed stabilization with no change in the cognitive memory score from baseline. The OCT scoring correlated with the stability of the MMSE score (Table 5). The subject appeared cognitively stable on clinical examinations during the 12-month study period. Short term memory loss without significant decline from baseline was observed during the 12-month study period.

Speech: Improvement of fluency of the patient's speech was observed. A shorter word finding latency time for his responses to direct questions was observed and his responses continued to be appropriate.

Mood/Behavior: Overall improvements in behavior at home, less agitation and emotional lability were noted. The patient did not have any reported suicidal ideation based upon monthly Columbia Suicide Severity Rating Scale ("CSSRS") assessments or reported or observed depressed mood during the 12-month study period.

TABLE 5

Patient's OCT and MMSE Score During Duration of Treatment

| Dose | Dose Amount (mg/kg) | MMSE Score | Clock Test Score |
|---|---|---|---|
| Baseline and Dose 1 | 500 | 25/30 | 53/100 |
| 2 | 500 | | 18/100 |
| 3 | 1000 | | 30/100 |
| 4 | 1000 | 24/30 | 24/100 |
| 5 | 1500 | | |
| 6 | 1500 | | |
| 7 | 500 | 24/30 | |
| 8 | 500 | | |
| 9 | 1000 | 25/30 | 76/100 |
| 10 | 750-500 | | |
| 11 | 750 | | |
| 12 | 750 | 26/30 | 62/100 |

(vii) Adverse Events Summary

An episode of diarrhea occurred upon completion of Month 0 (first infusion), mild in severity, and did not require medical intervention. The episode was possibly related to Trappsol® Cyclo™ HPβCD and exacerbation of the patient's medical history of Inflammatory Bowel Disease (IBS) with episodes of diarrhea. The episode was resolved approximately 1 day later.

Elevated blood pressure during the IV infusions was noted throughout course of the 12-month study period. Blood pressure elevations were asymptomatic and not clinically significant and blood pressure returned to baseline at completion of the infusions. The blood pressure data were reviewed with the patient's treating cardiologist and no change in concomitant medications was made per the cardiologist's recommendation.

A vasovagal episode occurred after completion of the Month 5 IV infusion during dose escalation to the 1500 mg/kg dose. The episode was moderate in severity. The patient was medically monitored for safety until resolution of symptoms and no medical intervention was required. The adverse event was possibly related to Trappsol® Cyclo™ HPβCD infusion, or exacerbation of underlying IBS. This adverse event was reviewed with the patient's cardiologist and was determined to be vasovagal as there was no evidence of cardiac ischemia noted during the event. The patient was followed regularly by his treating cardiologist and cleared for continued participation in the study treatments. The adverse event resolved spontaneously the same day. The adverse event was reviewed by Safety Review Committee and the dose was reduced per protocol for tolerability.

An episode of diarrhea occurred after completion of the Month 5 IV HPβCD infusion. The episode was mild in severity and did not require medical intervention. The episode was possibly related to IP or exacerbation of pre-existing IBS. The adverse event was resolved the same day without medical intervention.

Left wrist phlebitis was treated with a single dose of Keflex. The adverse event was mild severity and likely related to the Month 5 study procedures. The adverse event was resolved approximately 3 days later.

(viii) Biomarker Data

Oxysterol biomarker data was collected during the 12-month study period to determine effect of IV Trappsol® Cyclo™ HPβCD infusions on cholesterol synthesis pathway (Table 6).

The patient tolerated the 8-hour IV Trappsol® Cyclo™ HPβCD monthly infusions well without evidence of toxicity or safety issues. The patient showed cognitive and neurologic stability in serial examinations during the study. In persons with Alzheimer's disease dementia, there is an expected measurable cognitive and functional decline over a 12-month period. For the current patient, improvements in behavior were observed, indicating an improvement in quality of life benefit for this patient. The expected decline in cognition and memory that would be expected over a 12-month period in persons with Alzheimer's disease dementia was not observed in this patient.

EQUIVALENTS

The disclosure can be embodied in other specific forms with departing from the essential characteristics thereof. The foregoing embodiments therefore are to be considered illustrative rather than limiting on the disclosure described herein. The scope of the disclosure is indicated by the appended claims rather than by the foregoing description, and all changes that come within the meaning and range of equivalency of the claims are intended to be embraced therein.

What is claimed:

1. A method of treating Alzheimer's disease in a human patient suffering from Alzheimer's disease comprising administering an effective amount of a hydroxypropyl beta-cyclodextrin composition.

TABLE 6

Lathosterol, Lanosterol, Desmosterol, 24-S-hydroxycholesterol, 7-Ketocholesterol and cholestane-3β 5α 6β-triol Concentration for Biomarkers in Patient Serum

| Visit | Time Point | Lathosterol (µg/mL) | Lanosterol (µg/mL) | Desmosterol (µg/mL) | 24-S-hydroxycholesterol (ng/mL) | 7-Ketocholesterol (ng/mL) | Cholestane-3β 5α 6β-triol (ng/mL) |
|---|---|---|---|---|---|---|---|
| Day 0 | pre-dose | 1.90 | BLQ | 0.292 | 26.6 | 14.7 | 3.34 |
| Day 0 | 24 h | 2.11 | 0.132 | 0.371 | 27.4 | 9.96 | 2.10 |
| Day 0 | 48 h | 2.02 | 0.123 | 0.322 | 35.0 | 10.5 | 2.12 |
| Day 0 | 72 h | 1.96 | 0.124 | 0.315 | 23.3 | 9.69 | 2.26 |
| Month 1 | pre-dose | 2.18 | 0.112 | 0.286 | 25.1 | 9.60 | 2.46 |
| Month 1 | 24 h | 2.37 | 0.136 | 0.312 | 24.6 | 11.2 | 2.45 |
| Month 1 | 48 h | 2.46 | 0.127 | 0.292 | 25.9 | 7.94 | 3.93 |
| Month 1 | 72 h | 3.00 | 0.180 | 0.356 | 27.7 | 7.23 | 2.54 |
| Month 2 | pre-dose | 1.80 | BLQ | 0.230 | 28.8 | 7.65 | 2.06 |
| Month 2 | 24 h | 1.93 | BLQ | 0.274 | 29.0 | 4.64 | 2.10 |
| Month 2 | 48 h | 1.67 | BLQ | 0.258 | 31.7 | 5.84 | 2.74 |
| Month 2 | 72 h | 1.53 | 0.108 | 0.253 | 30.9 | 6.31 | 3.33 |
| Month 3 | pre-dose | 1.79 | 0.105 | 0.206 | 32.9 | 8.69 | 11.4 |
| Month 3 | 24 h | 1.64 | BLQ | 0.213 | 37.9 | 8.22 | 8.93 |
| Month 3 | 48 h | 1.73 | BLQ | 0.201 | 32.0 | 7.27 | 12.0 |
| Month 3 | 72 h | 1.68 | 0.126 | 0.206 | 33.5 | 8.82 | 13.7 |
| Month 4 | pre-dose | 2.21 | 0.120 | 0.204 | 25.0 | 11.6 | 10.2 |
| Month 4 | 24 h | 1.41 | 0.102 | 0.219 | 31.2 | 6.95 | 6.65 |
| Month 4 | 48 h | 1.78 | 0.135 | 0.227 | 32.0 | 8.51 | 7.76 |
| Month 4 | 72 h | 1.74 | 0.127 | 0.205 | 35.3 | 10.3 | 8.41 |
| Month 5 | pre-dose | 1.23 | BLQ | 0.110 | 15.3 | 19.7 | 12.1 |
| Month 5 | (No timepoint) | 1.78 | 0.160 | 0.243 | 21.4 | 26.5 | 11.3 |
| Month 7 | pre-dose | 1.70 | 0.124 | 0.246 | 19.3 | 18.7 | 8.69 |
| Month 7 | 24 h | 1.74 | 0.123 | 0.303 | 21.0 | 28.2 | 10.4 |
| Month 8 | pre-dose | 1.51 | 0.109 | 0.227 | 26.0 | 25.7 | 8.85 |
| Month 8 | 24 h | 1.55 | 0.111 | 0.237 | 28.5 | 18.7 | 8.30 |
| Month 9 | Control B | 2.70 | 0.271 | 0.876 | 18.3 | 12.7 | 6.58 |
| Month 9 | Control A | 2.76 | 0.286 | 0.869 | 15.4 | 6.13 | 3.23 |
| Month 9 | pre-dose | 1.58 | 0.110 | 0.177 | 22.3 | 11.9 | 5.26 |
| Month 9 | 24 h | 1.74 | BLQ | 0.198 | 24.6 | 7.06 | 4.70 |
| Month 10 | pre-dose | 1.57 | BLQ | 0.210 | 29.6 | 22.7 | 17.2 |
| Month 10 | 24 h | 1.60 | BLQ | 0.255 | 26.2 | 29.6 | 22.9 |
| Month 11 | pre-dose | 1.44 | 0.103 | 0.165 | 32.2 | 25.8 | 19.7 |
| Month 11 | 24 h | 1.15 | 0.105 | 0.164 | 37.9 | 58.3 | 30.7 |

2. The method according to claim 1, wherein the patient has progression of the Alzheimer's disease after previous administration of another therapy.

3. The method according to claim 2, wherein the previous administration of another therapy is a therapy for Alzheimer's disease.

4. The method according to claim 1, wherein the human patient is at least 50 years old.

5. The method according to claim 1, wherein the human patient is at least 60 years old.

6. The method according to claim 1, wherein the human patient is at least 65 years old.

7. The method according to claim 1, wherein the human patient is at least 70 years old.

8. The method according to claim 1, wherein the human patient is at least 80 years old.

9. The method according to claim 1, further comprising administering the hydroxypropyl-beta-cyclodextrin composition in a monthly dose amount of about 500 mg/kg to about 1500 mg/kg.

10. The method according to claim 9, wherein the monthly dose amount is from about 500 mg/kg to about 1000 mg/kg.

11. The method according to claim 1, wherein the hydroxypropyl-beta-cyclodextrin composition is administered by parenteral administration.

12. The method according to claim 1, further comprising administering the hydroxypropyl-beta-cyclodextrin composition in a monthly dose amount of about 100 mg to about 750 mg.

13. The method according to claim 12, wherein the hydroxypropyl-beta-cyclodextrin composition is administered by central nervous system (CNS) directed administration.

14. The method according to claim 1, wherein the hydroxypropyl-beta-cyclodextrin composition is administered once a month.

15. The method according to claim 1, wherein the hydroxypropyl-beta-cyclodextrin composition is administered twice a month.

16. The method according to claim 1, wherein the hydroxypropyl-beta-cyclodextrin composition is administered weekly.

17. The method according to claim 10, wherein the hydroxypropyl-beta-cyclodextrin composition is administered intravenously.

18. The method according to claim 10, wherein the hydroxypropyl-beta-cyclodextrin composition is administered subcutaneously.

19. The method according to claim 10, wherein the hydroxypropyl-beta-cyclodextrin composition is administered by intrathecal administration.

20. The method according to claim 10, wherein the hydroxypropyl-beta-cyclodextrin composition is administered by intracerebroventricular administration.

21. The method according to claim 1, wherein the hydroxypropyl-beta-cyclodextrin composition comprises a 25% (w/v) solution of one or more hydroxypropyl-beta-cyclodextrin species.

22. The method according to claim 1, further comprising administering the hydroxypropyl-beta-cyclodextrin composition in a monthly escalating dose regimen until a maximum tolerated dose is determined, and subsequently administering the maximum tolerated dose.

23. The method according to claim 1, further comprising administering the hydroxypropyl-beta-cyclodextrin composition monthly for at least 12 months.

24. The method according to claim 1, further comprising administering a second therapeutic agent selected from the group consisting of donepezil, rivastigmine, galantamine, memantine, verubecestat, solanezumab, bapineuzumab, aducanumab, tideglusib, epothilone D and ABBV-8E12.

25. The method according to claim 1, further comprising administering a second therapeutic agent selected from the group consisting of a cholinesterase inhibitor, an NMDA receptor antagonist, a humanized antibody which targets tau protein, a humanized antibody which targets amyloid beta protein, and a BACE inhibitor.

26. The method according to claim 1, further comprising administering a second therapeutic agent, wherein the second therapeutic agent is selected from any therapeutic agent set forth in Table 1.

27. The method according to claim 1, wherein the hydroxypropyl-beta-cyclodextrin composition comprises a mixture of two or more hydroxypropyl-beta-cyclodextrin species, wherein each of the two or more hydroxypropyl-beta-cyclodextrin species has a different degree of hydroxypropylation of the beta-cyclodextrin ring, and wherein the mixture of two or more hydroxypropyl-beta-cyclodextrin species has a molar substitution value from about 0.59 to about 0.73.

28. The method according to claim 1, wherein the hydroxypropyl-beta-cyclodextrin composition comprises 2.5% w/w or less of propylene glycol.

29. The method according to claim 1, wherein the hydroxypropyl-beta-cyclodextrin composition comprises a mixture of two or more hydroxypropyl-beta-cyclodextrin species, wherein each of the two or more hydroxypropyl-beta-cyclodextrin species has a different degree of hydroxypropylation of the beta-cyclodextrin ring, and wherein the hydroxypropyl-beta-cyclodextrin composition comprises 0.15% w/w or less of unsubstituted beta-cyclodextrin.

30. The method according to claim 1, wherein the hydroxypropyl-beta-cyclodextrin composition comprises a mixture of two or more hydroxypropyl-beta-cyclodextrin species, wherein each of the two or more hydroxypropyl-beta-cyclodextrin species has a different degree of hydroxypropylation of the beta-cyclodextrin ring, wherein the mixture of two or more hydroxypropyl-beta-cyclodextrin species has a molar substitution value from about 0.59 to about 0.73, and wherein the hydroxypropyl-beta-cyclodextrin composition comprises 2.5% w/w or less of propylene glycol and 0.15% w/w or less of unsubstituted beta-cyclodextrin.

31. A method of treating Alzheimer's disease in a human patient suffering from Alzheimer's disease, the method comprising administering to the human patient an effective amount of a hydroxypropyl beta-cyclodextrin composition, wherein the hydroxypropyl-beta-cyclodextrin composition comprises a mixture of two or more hydroxypropyl-beta-cyclodextrin species, and wherein the mixture of two or more hydroxypropyl-beta-cyclodextrin species has a molar substitution value from about 0.59 to about 0.73.

32. A method of treating Alzheimer's disease in a human patient suffering from Alzheimer's disease, the method comprising:
 (a) administering to the human patient an initial 500 mg/kg dose by parenteral administration or an initial dose of 100 mg by CNS directed administration, of a hydroxypropyl-beta-cyclodextrin composition; and
 (b) administering to the human patient the hydroxypropyl-beta-cyclodextrin composition in a monthly escalating dose regimen until a maximum tolerated dose is determined.

33. The method of claim 32, further comprising administering the maximum tolerated dose of the hydroxypropyl beta-cyclodextrin composition once a month for 3 months, 4 months, 5 months, 6 months, 7 months, 8 months, 9 months, 10 months, 11 months, or 12 months.

34. The method of claim 32, further comprising administering the maximum tolerated dose of the hydroxypropyl-beta-cyclodextrin composition once a month for up to the duration of the life span of the human patient.

35. A method of treating Alzheimer's disease in a human patient suffering from Alzheimer's disease comprising administering a hydroxypropyl beta-cyclodextrin composition to the patient wherein the monthly dose amount is 500 mg/kg.

36. The method according to claim 35 wherein the hydroxypropyl-beta-cyclodextrin composition is administered by parenteral administration.

37. A method of treating Alzheimer's disease in a human patient suffering from Alzheimer's disease comprising administering a hydroxypropyl beta-cyclodextrin composition to the patient wherein the monthly dose amount is 1000 mg/kg.

38. The method according to claim 37 wherein the hydroxypropyl-beta-cyclodextrin composition is administered by parenteral administration.

* * * * *